United States Patent [19]

Tagawa et al.

[11] Patent Number: 4,939,255
[45] Date of Patent: Jul. 3, 1990

[54] HEXA-CYCLIC CAMPTOTHECIN DERIVATIVES

[75] Inventors: Hiroaki Tagawa; Masamichi Sugimori; Hirofumi Terasawa; Akio Ejima; Satoru Ohsuki, all of Tokyo, Japan

[73] Assignees: Daiichi Pharmaceutical Co., Ltd.; Kabushiki Kaisha Yakult Honsha, both of Tokyo, Japan

[21] Appl. No.: 207,718

[22] Filed: Jun. 16, 1988

[30] Foreign Application Priority Data

Jun. 24, 1987 [JP] Japan .................. 62-156990
Jan. 13, 1988 [JP] Japan .................. 63-005503

[51] Int. Cl.$^5$ ........................... C07D 491/22
[52] U.S. Cl. ............................ 540/578; 540/581; 544/361; 544/362; 544/125; 546/41; 546/48; 546/51
[58] Field of Search ............... 546/41, 48, 51; 544/362, 361, 125; 540/477, 578, 581

[56] References Cited

U.S. PATENT DOCUMENTS

| Re. 32,518 | 10/1987 | Miyasaka et al. | 546/48 |
| 4,473,692 | 9/1984 | Miyasaka et al. | 546/48 |
| 4,513,138 | 4/1985 | Miyasaka et al. | 546/48 |
| 4,545,880 | 10/1985 | Miyasaka et al. | 204/158 R |
| 4,604,463 | 8/1986 | Miyasaka et al. | 544/125 |

FOREIGN PATENT DOCUMENTS

| 220601 | 5/1987 | European Pat. Off. | |
| 0296597 | 12/1988 | European Pat. Off. | 546/41 |
| 0325247 | 7/1989 | European Pat. Off. | 546/48 |
| 0051288 | 3/1984 | Japan | 546/48 |

OTHER PUBLICATIONS

Honsha Co. Ltd., Chem. Abs., vol. 97 entry, 97: 188278b, (1982).

Organic Reactions, 28, 37–201, John Wiley & Sons, Inc. New York (1982).
C. F. Schwender et al., J. Med. Chem., 16, 254–257, (1973).
A. Ricci et al., J. Heterocyclic Chem. 11, 515–518, (1974).
C. F. Schwender et al., J. Med. Chem., 16, 254–257, (1973).

Primary Examiner—Mukund J. Shah
Assistant Examiner—Andrew G. Rozycki
Attorney, Agent, or Firm—Oblon, Spivak, McClelland, Maier & Neustadt

[57] ABSTRACT

A novel hexa-cyclic compound, a derivative of camptothecin, of the general formula:

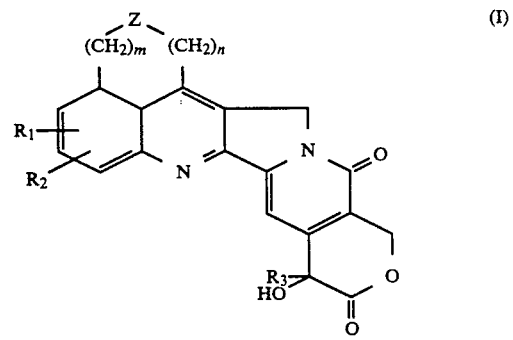

The compound is prepared from an aminoketone compound and a pyranoindolizine compound through Friedlaender reaction. It has an excellent antitumor activity and a high degree of safety, and can be applied as an antitumor medicine for curing tumors of various kinds.

3 Claims, No Drawings

HEXA-CYCLIC CAMPTOTHECIN DERIVATIVES

BACKGROUND OF THE INVENTION

1. Field of the Invention

This invention relates to a novel compound having an antitumour activity and a process for preparing this compound.

2. Description of the Background

Camptothecin is a penta-cyclic alkaloid isolated from barks, roots, fruits, or leaves of camptotheca acuminata. This compound is known to exhibit an antitumour activity because of its capability of inhibiting nucleic acid synthesis. According to the results of clinical tests conducted in the United States, however, the compound was found to have a problem in view of safety, and its research and development as a medicine have been discontinued.

Thereafter, research on derivatives of camptothecin possessing better activity and reduced toxicity has been undertaken worldwide. However, no report has surfaced on the derivative with satisfactory clinical results.

The present inventors have conducted extensive studies for the purpose of obtaining camptothecin derivatives with compounds with activities superior to that of camptothecin. This finding has led to the completion of this invention.

SUMMARY OF THE INVENTION

Accordingly, an object of this invention is to provide a hexa-cyclic compound represented by the following general formula:

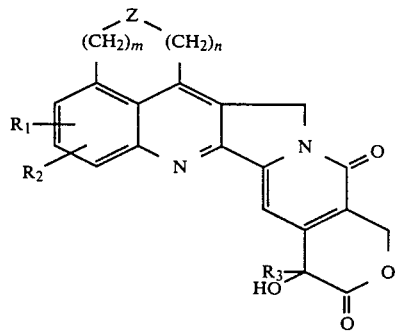

wherein $R_1$ and $R_2$ independently represent hydrogen atoms, hydroxyl groups, $C_{1-6}$ alkyl groups, $C_{1-6}$ alkenyl groups, $C_{1-6}$ alkynyl groups, $C_{1-6}$ alkoxyl groups, $C_{1-6}$ aminoalkoxyl groups, halogen atoms, nitro groups, cyano groups, mercapto groups, $C_{1-6}$ alkylthio groups, $C_{1-6}$ hydroxyalkyl groups, $C_{1-6}$ halogenoalkyl groups, $C_{1-6}$ cyanoalkyl groups, $C_{1-6}$ nitroalkyl groups, $C_{1-6}$ aminoalkyl groups which may contain protective groups or $C_{1-6}$ alkyl groups, $C_{1-6}$ aminoalkylamino groups which may contain protective groups or $C_{1-6}$ alkyl groups at the amino-position, heterocyclic $C_{1-6}$ alkyl groups which may contain $C_{1-6}$ alkyl, $C_{1-6}$ alkoxyl, amino, halogeno, nitro, or cyano groups, heterocyclic $C_{1-6}$ alkylamino groups which may contain $C_{1-6}$ alkyl, $C_{1-6}$ alkoxyl, amino (which may contain protective groups), halogeno, nitro, cyano groups, or protective groups, amino-heterocyclic groups which may contain protective groups or $C_{1-6}$ alkyl groups at the nitrogen atom of the heterocyclic ring moiety or amino position, heterocyclic-amino groups which may contain protective groups or $C_{1-6}$ alkyl groups at the nitrogen atom of the heterocyclic ring moiety or amino position, carbamoyl groups which may contain protective groups or $C_{1-6}$ alkyl groups, heterocyclic carbonyl groups which may contain $C_{1-6}$ alkyl, $C_{1-6}$ alkoxyl, amino, hydroxyl, halogeno, nitro, or cyano groups, $R_3$ represents an $C_{1-6}$ alkyl group, Z represents O, S, CH-$R_4$ ($R_4$ stands for a hydrogen atom or a $C_{1-6}$ alkyl group), or N-$R_5$ ($R_5$ stands for a hydrogen atom, a $C_{1-6}$ alkyl group, or a protective group for the amino group), and m and n independently represent 0, 1 or 2.

Another object of this invention is to provide a process for preparing the compound represented by the above formula (I).

Other objects, features and advantages of the invention will hereinafter become more readily apparent from the following description.

DETAILED DESCRIPTION OF THE INVENTION AND PREFERRED EMBODIMENTS

In the definition of $R_1$, $R_2$, $R_3$, $R_4$, and $R_5$ of the compound represented by formula (I), the number of carbon atoms of said alkyl, alkenyl, alkynyl, or alkoxy group, with or without a functional substituent group such as amino, hydroxyl, halogeno, thio, or heterocyclic group is in the range of 1 to 6, and the term "heterocyclic" means a substituent derived from a heterocyclic compound, and having carbon atoms of 4 to 7 and hetero atoms of 1 to 3 selected from the group consisting of nitrogen, oxygen and sulfur.

The numbering of the ring-constituent atoms and the designation of the rings A to F are defined as shown in the following formula IA:

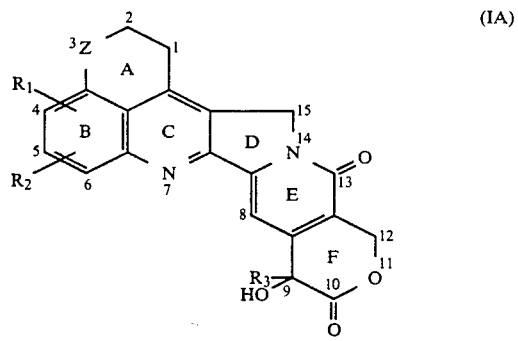

in which Z represents —CH$_2$—, —O—, —S—, —NH—, or —N(acyl)—, $R_3$ represents an ethyl group. As for the configuration around the asymmetric carbon at 9 position, S-configuration (for the substituent on F-ring) is more preferable from the view point of antitumour activity.

When $R_1$, $R_2$, $R_3$, or $R_4$ is an alkyl, alkenyl, or alkynyl group, the compound having the $R_1$ or $R_2$ of from 1 to 6 carbon atoms, especially ethyl group, methyl group, or the like, is desirable.

Given as examples of protective groups for an amino group are formyl, acetyl, trityl, tert-butoxycarbonyl, p-methoxybenzyloxycarbonyl, and the like.

A heterocyclic ring includes, for instance, groups derived from azetidine, pyrrolidine, piperidine, piperazine, imidazoline, morpholine, and the like.

More specific examples of $R_1$ and $R_2$ include methyl, ethyl, hydroxyl, methoxy, chloro, bromo, nitro, amino, hydrazino, aminomethyl, aminoethyl, aminoethoxy, dimethylhydrazino, (pyrrolidine-3-yl)amino, (morphorine-1-yl)amino, 2-aminoethylamino, 2-dimethylaminoethylamino, piperidine-1-yl, 4-aminopiperidine-1-yl, piperazine-1-yl, 4-methylpiperazine-1-yl, 4-aminopiperazine-1-yl, piperazine-1-yl-amino, 4-methylpiperazine-1-yl-amino, 4-aminopiperazine-1-yl-amino, and the like.

The compound of this invention can be prepared by the method exemplified by the following reaction scheme:

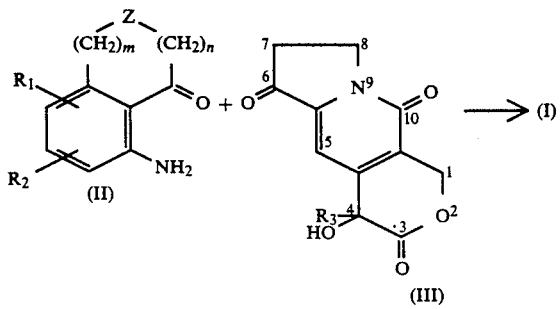

Specifically, an aminoketone compound II and pyranoindolizine compound III (European Patent Publication No. 0220601-A) are condensed by Friedlaender reaction [*Organic Reactions*, 28, 37-202, John Wiley & Sons, Inc., New York (1982)] to produce the compound (I).

Aminoketone compounds (II) are known compounds and can be readily prepared according to the methods known in the art.

The conditions of this condensation ring-closing reaction of the compounds (II) and (III) can be suitably selected from the conditions, wherein the reaction is conducted at room temperature or an elevated temperature in the presence of an acid or a base.

It is desirable to effect the reaction in the presence of a solvent. There is no specific limitation to the kind of the solvent used, so long as the solvent is inert to the reaction. Examples of the solvent which can be used include aromatic hydrocarbons such as benzene, toluene, xylene, and the like, halogenated hydrocarbons such as dichloromethane, chloroform, 1,1-dichloroethane, 1,2-dichloroethane, and the like, ethers such as diethyl ether, diisopropyl ether, tetrahydrofuran, dimethyl cellosolve, diethyl cellosolve, diglyme, and the like, lower alcohols such as methanol, ethanol, propanol, tert-butanol, and the like, amides such as acetamide, dimethylacetamide, N,N-dimethylformamide, and the like, and acetic acid. Preferable solvents are benzene, toluene, and acetic acid.

A base to be employed in the reaction may be either an inorganic or organic base. Given as examples of inorganic bases are hydroxides, carbonates, and bicarbonates of alkali metal such as lithium hydroxide, sodium hydroxide, potassium hydroxide, lithium carbonate, sodium carbonate, potassium carbonate, sodium bicarbonate, potassium bicarbonate, and the like. Sodium hydride can also be employed. Organic base include alkoxide of alkali metal such as sodium methoxide, sodium ethoxide, potassium tert-butoxide, and the like, tert-alkyl amines such as triethylamine, N,N-diisopropylethylamine, and the like, aromatic tertiary amines such as N,N-dimethyl aniline, N,N-diethyl aniline, N,N-dimethyl aminopyridine, and the like, pyridine, 1,8-diazabicycloundecene, and the like. Preferred bases are potassium carbonate and triethylamine. Compound (III) in some cases is unstable under alkaline conditions. Deliberate consideration therefore must be given to the reaction conditions when a base is used. For example, measures must be taken such as carrying out the reaction at a relatively low temperature, for a shorter period of time, or under acidic conditions.

The reaction is carried out at a temperature usually of 20°-150° C., and preferably 80°-120° C. Depending on the stability of compound (III), however, effecting the reaction under ice-cooling is desirable.

The reaction time may be between 1 hour to 48 hours. Usually, the reaction is completed within 1-24 hours.

A typical example of performing the reaction is refluxing the reaction mixture in benzene or toluene in the presence of p-toluene sulfonic acid, or refluxing in acetic acid.

Protective groups of an amino group can be removed by reduction or hydrolysis with an acid or alkali, if present in $R_1$, $R_2$, or $R_5$.

Compounds having an alkoxyl group can be converted into the hydroxyl compounds by treating them with aluminum chloride or aluminum bromide in an inert solvent such as toluene, benzene, or the like, or by heating with hydrobromic acid.

A compound having a nitro group can be converted into the corresponding amino compound by catalytic reduction using the catalyst of platinum, palladium, or the like.

A compound having an amino group can be converted into corresponding hydroxyl compound via a diazonium compound by the treatment with sodium nitrite or the like, followed by hydrolysis of the diazonium salt.

A compound having an amino group can also be converted into the corresponding halogeno compound by Sandmeyer reaction via diazonium salt mentioned above. General Sandmeyer reaction conditions can be applicable to this reaction using cuprous chloride, cuprous bromide, or the like.

The compound of this invention can be converted into a form of physiologically acceptable salt, after having been converted, as desired, into a salt of an alkali metal or alkali earth metal using a hydroxide of these metals, or when such a compound is a basic compound such as that possessing an amino group or the like, into an inorganic or organic salt using an inorganic acid such as hydrochloric acid, sulfuric acid, phosphoric acid, or the like, or an organic acid such as formic acid, acetic acid, or the like.

Antitumour effects of the compound of this invention thus prepared are hereinafter described by way of experimental examples

Experimental Example 1

P388 murine leukemia cells ($1 \times 10^6$/mouse) were inoculated into male CDF-1 mice (5-6 mice per group, age 7-10 weeks, weighing 21-34 g) on day 0, and the test compound was administered intraperitoneally on day 1.

The test compound were dissolved in water or physiological saline after having been converted into sodium salts, or suspended into a physiological saline containing 0.9% benzyl alcohol, 0.4% Tween 80, or 0.5% CMC.

The antitumour effect was evaluated by the percentage of the median survival time of the treated group (T) against that of the control group (C). The results are shown in the table below.

| | Amount Administered (mg/kg) | T/C (%) | Mice Survived for 40 days (Out of 6) |
|---|---|---|---|
| Compound of Example 1 | 240 | >392 | 5 |
| Compound of Example 2 | 480 | >376 | 4 |
| Compound of Example 3 | 480 | >400 | 5 |
| Compound of Example 16 | 60 | 443 | 4 |

Experimental Example 2

A test compound was added to a suspension containing P388 mouse leukemia cells ($2 \times 10^4$/ml) and the cells were cultured in 5% $CO_2$ at 30° C. After 72 hours, the number of the cells were counted to determine the $IC_{50}$ value. The results are listed in the following table.

| | $IC_{50}$ (nMol/ml) |
|---|---|
| Compound of Example 1 | 1.47 |
| Compound of Example 2 | 0.81 |
| Compound of Example 3 | 4.32 |
| Compound of Example 4 | 3.73 |
| Compound of Example 5 | 3.30 |
| Compound of Example 8 | 3.03 |
| Compound of Example 11 | 2.64 |
| Compound of Example 16 | 7.23 |
| Compound of Example 20 | 0.92 |
| Compound of Example 21 | 3.41 |

As is evident from the results of these experiments, the compound of this invention has an excellent antitumour activity and a high degree of safety, and thus can be applied as an antitumour medicine for curing tumors of various kinds.

The compound can be administered orally, by way of injection, inclusive of intravenous injection, intramuscular injection, or subcutaneous injection, or by any other suitable means. Among these, preferable means are intravenous injection or oral administration in a form of aqueous preparation. An aqueous preparation may be prepared by converting the compound into an acid adduct with a pharmacologically acceptable acid, when the compound has an amine substituent, or by converting it into a salt of an alkali metal such as sodium salt, when it is a compound without an amine substituent. When the compound is orally administered, it can be either free or in the form of a salt.

A suitable dosing form of an antitumour medicine comprising the compound of this invention is selected from various kinds, and the same is prepared according to methods conventionally employed in preparing such a form of medicine. The dosing forms for oral administration may include tablets, dispersions, granules, capsules, liquids, syrups, elixir, oily or aqueous suspensions, and the like.

Injections may contain in its preparation stabilizers, preservatives, or solubilizing adjuvant. The solution of the compound which may contain these ingredients is put into a container and solidified by means of lyophilization, for example. This lyophilized formulation is then put into a injection dosing form when administered. The container may contain either a dose for one injection or multiple doses.

A fluid preparation can be a solution, suspension, emulsion, or the like which may contain additives such as suspending agents, emulsifier, or the like.

A dose of the antitumour compound of this invention is usually in the range of 10 mg–1 g/adult/day, and preferably of 200–400 mg/adult/day.

The proportion of the compound of this invention contained in a preparation is 0.1% or more, and preferably is 1–50%.

Other features of the invention will become apparent in the course of the following description of the exemplary embodiments which are given for illustration of the invention and are not intended to be limiting thereof.

EXAMPLES

EXAMPLE 1

Preparation of 9-ethyl-2,3-dihydro-4,9-dihydroxy-1H,12H-benzo[de]-pyrano[3',4':6,7]indolizino[1,2-b]quinoline-10,13(9H,15H)-dione: (in formula IA, Z=—$CH_2$—, $R_1$=4—OH, $R_2$=H, and $R_3$=Et)

Into 120 ml of acetic acid 1.44 g of 8-amino-3,4-dihydro-5-hydroxy-1(2H)-naphthalenone-hydrochloride [in formula II, Z=—$CH_2$—, m=0, n=2, $R_1$=5—OH, $R_2$=H; C. F. Schwender et al., *J. Med. Chem.*, 16, 254–257 (1973)] and 1.94 g of 7,8-dihydro-4-ethyl-4-hydroxy-1H-pyrano[3,4-f]indolizine-3,6,10(4H)-trione (in formula III, $R_3$=Et) were dissolved and the solution was stirred at 100° C. for 11 hours. After cooling, the insoluble material was collected by filtration, and washed with ethyl acetate and ethanol successively. The residue was dissolved in 240 ml of 0.6 N sodium hydroxide. The solution was washed with dichloromethane and ethyl acetate, and adjusted to pH 1 with hydrochloric acid. The precipitate was collected by filtration, and washed with water and methanol to obtain 1.35 g of the title compound.

mp: 270°–280° C. (dec.)

NMR (DMSO-$d_6$) δ: 0.89 (3H, t, J=7.0 $H_z$, $CH_3$), 1.6–2.3 (4H, m, $C_2$—H, $CH_3\underline{CH_2}$), 2.7–3.3 (4H, m, $C_1$—H, $C_3$—H), 5.20 (2H, s, $C_{15}$—H), 5.41 (2H, s, $C_{12}$—H), 7.27 (1H, s, $C_8$—H), 7.48 (1H, d, J=9.2 H=, $C_5$—H), 7.85 (1H, d, J=9.2 $H_z$, $C_6$—H,)

IR $\nu_{max}^{KBr}$ cm$^{-1}$: 3424, 1758, 1653, 1587

Elemental analysis for $C_{23}H_{20}N_2O_5 \cdot 2/3H_2O$:
Calculated: C 66.34; H 5.16; N 6.73;
Found : C 66.38; H 5.17; N 6.75;

EXAMPLE 2

Preparation of 9-ethyl-1,2-dihydro-9-hydroxy-4-methyl-12H-pyrano[4,3,2-de]pyrano[3',4':6,7]indolizino[1,2-b]-quinoline-10,13 (9H,15H)-dione: (in formula IA, Z=—O—, $R_1$=4—Me, $R_2$=H, and $R_3$=Et)

To 150 ml of acetic acid were added 644 mg of 5-amino-8-methyl-4-chromanone (in formula II, Z=—O—, m=0, n=2, $R_1$=8—Me, $R_2$=H; C. A., Vol. 60, 9236g) and 857 mg of 7,8-dihydro-4-ethyl-4-hydroxy-1H-pyrano[3,4-f]indolizine-3,6,10(4H)-trione and the mixture was stirred at 100° C. for 12 hours. After distilling off about ⅔ of the solvent, chloroform and acetic acid were added successively to the reaction mixture, and the insoluble material was collected by filtration. The residue was washed with chloroform, methanol, and water to yield 322 mg of the title compound.

mp: 284°-300° C. (dec.)

NMR (DMSO d$_6$) δ: 0.88 (3H, t, J=7.2 Hz, C$\underline{H_3}$CH$_2$), 1.89 (2H, q, J=7.2 Hz, CH$_3$C$\underline{H_2}$), 2.36 (3H, s, CH$_3$—C$_4$), 2.54 (2H, t, J=5.4 Hz, C$_1$—H), 4.53 (2H, t, J=5.4 Hz, C$_2$—H), 5.25 (2H, s, C$_{15}$—H), 5.44 (2H, s, C$_{12}$—H), 6.51 (1H, s, OH), 7.31 (1H, s, C$_8$—H), 7.66 (2H, s, C$_5$—H, C$_6$—H)

IR ν$_{max}^{KBR}$ cm$^{-1}$: 3406, 1743, 1659, 1614

Elemental analysis for C$_{23}$H$_{20}$N$_2$O$_5$:
Calculated: C 68.31; H 4.98; N 6.93;
Found: C 68.02; H 5.03; N 6.86.

EXAMPLE 3

Preparation of
9-ethyl-1,2-dihydro-9-hydroxy-4-methyl-12H-thiino[4,3,2-de]pyrano3',4':6,7]indolizino[1,2-b]quinoline-10,13(9H,15H)-dione: (in formula IA, Z=—S—, R$_1$=4-Me, R$_2$=H, and R$_3$=Et)

To 100 ml of toluene 1.82 g of 5-amino-8-methyl-4-thiochromanone [in formula II, Z=—S—, m=0, n=2, R$_8$=8-Me, and R$_2$=H; A. Rui et al., *J. Heterocyclic Chem.*, 11, 515–518 (1974)] and 2.22 g of 7,8-dihydro-4-ethyl-4-hydroxy-1H-pyrano[3,4-f]indolizine-3,6,10(4H)-trione were added and the mixture was heated under reflux using a Deanstark apparatus for 30 minutes. To the mixture was added 700 mg of p-toluene sulfonic acid and the mixture was heated under stirring for further 7.5 hours. After cooling, a precipitate was collected by filtration and was washed with water, ethanol, ethyl acetate, and ether successively, and dried to yield 2.0 g of the title compound which was the powder having a pistachio color.

mp: above 300° C. (dec.)

NMR (DMSO d$_6$) δ: 0.88 (3H, t, J=7.0 Hz, CH$_3$C$\underline{H_2}$), 1.89 (2H, q, J=7.0 Hz, CH$_3$C$\underline{H_2}$), 2.43 (3H, s, CH$_3$—C$_4$), 3.2-3.6 (4H, m, C$_1$—H & C$_2$—H), 5.24 (2H, s, C$_{12}$—H or C$_{15}$—H), 5.47 (2H, s, C$_{15}$—H or C$_{12}$—H), 7.33 (1H, s, C$_8$—H), 7.67 (1H, d, J=9.0 Hz, C$_6$—H), 7.86 (1H, d, J=9.0 Hz, C$_5$—H), IR ν$_{max}^{KBr}$ cm$^{-1}$: 3300, 1746, 1653, 1599, 1557

Elemental analysis for C$_{23}$H$_{20}$H$_2$O$_4$S:
Calculated: C 65.70; H 4.79; N 6.66;
Found : C 65.58; H 4.87; N 6.57.

EXAMPLE 4

Preparation of
9-ethyl-1,2-dihydro-9-hydroxy-4-methyl-3H,12H-pyrano[3',4':6,7]indolizino[1,2-c]benzo[ij][2,7]-naphthilidine-10,13(9H,15H)-dione: (in formula IA, Z=—NH—, R$_1$=4-Me, R$_2$=H, and R$_3$=Et)

(1) 3-(2-methyl-5-nitroanilino)propionic acid:

In 300 ml of acetonitrile 60 g of 4-nitro-o-toluidine was dissolved. To the solution 25 ml of β-propiolactone was added dropwise in about 30 minutes while heating under reflux. The refluxing was continued for further 3.5 hours. After cooling, the solvent was distilled off from the reaction mixture. The residue obtained was dissolved in 1 liter of 10% sodium hydroxide aqueous solution and the solution was washed twice with ether. The aqueous layer was adjusted to pH 2 by adding concentrated hydrochloric acid. The deposited crystals were collected by filtration, washed with water, and dried to yield 36.4 g of the title compound as yellow crystals.

mp: 192°-195° C.

NMR (DMSO d$_6$) δ: 2.17 (3H, s, CH$_3$), 2.59 (2H, t, J=6.5 Hz, C$_2$—H), 3.42 (2H, br, t, J=6.5 Hz, C$_3$—H), 5.4–5.7 (1H, m, N—H), 7.20 (1H, d, J=9.0 Hz, C$_3'$—H), 7.26 (1H, d, J=2.0 Hz, C$_6'$—H), 7.40 (1H, dd, J=9.0 Hz, 2.0 Hz, C$_4'$—H)

(2) 3-(5-amino-2-methylanilino)propionic acid:

In 140 ml of a mixed solvent of ethanol and dioxane (1:1) 5.2 g of the compound prepared in (1) above was dissolved. To the solution was added 150 mg of platinic oxide and the mixture was catalytically hydrogenated. After removing the catalyst by filtration, the filtrate was evaporated to dryness to yield 4.61 g of the title compound as a light brown powder.

NMR (DMSO-d$_6$) δ: 1.89 (3H, s, CH$_3$), 2.52 (2H, t, J=7.2 Hz, C$_2$—H), 3.22 (2H, t, J=7.2 Hz, C$_3$—H), 5.79 (1H, dd, J=8.0 Hz, 2.0 Hz, C$_4'$—H), 5.88 (1H, d, J=2.0 Hz, C$_6'$—H), 6.60 (1H, d, J=8.0 Hz, C$_3'$—H)

(3) 5-amino-8-methyl-2,3-dihydroquinolin-4(1H)-one:

Polyphosphoric acid weighing 80 g was heated to 100°-110° C., to which 4.6 g of the compound prepared in (2) above was gradually added to dissolve while stirring. The mixture was cooled and charged into ice water, adjusted to pH 11 with 10% sodium hydroxide aqueous solution, and extracted with chloroform. The extract was washed with water and saturated sodium chloride aqueous solution and dried over anhydrous sodium sulfate. The solvent was removed under reduced pressure. The residue was purified with silica gel column chromatography using ethyl acetate-hexane (4:6) as an eluent. After removing the solvent, from the fractions containing the target compound, 2.24 g of the title compound was obtained as a red-yellow oil.

NMR (DMSO d$_6$) δ: 1.92 (3H, s, CH$_3$), 2.59 (2H, t, J=7.0 Hz, C$_3$—H), 3.48 (2H, t, J=7.0 Hz, C$_2$—H), 5.80 (1H, d, J=9.0 Hz, C$_6$—H), 6.83 (1H, d, J=9.0 Hz, C$_7$—H)

(4) 5-benzyloxycarbonylamino-8-methyl-2,3-dihydroquinolin-4(1H)-one:

In 10 ml of benzene 266 mg of the compound prepared in (3) above was dissolved. To the solution were added 0.22 ml of benzyloxycarbonyl chloride and 0.13 ml of pyridine, and the mixture was stirred at room temperature for 1 hour. The reaction mixture was washed with water and saturated sodium chloride aqueous solution and dried over anhydrous sodium sulfate. The residue was purified with silica gel column chromatography using ethyl acetate-hexane (1:2) as an eluent to yield 402 mg of the title as yellow crystals.

NMR (CDCl$_3$) δ: 2.08 (3H, s, CH$_3$), 2.78 (2H, t, J=7.7 Hz, C$_3$—H), 3.58 (2H, t, J=7.7 Hz, C$_2$—H), 5.19 (2H, s, Ph—CH$_2$—), 7.14 (1H, d, J=8.5 Hz, C$_6$—H), 7.1–7.6 (5H, m, —Ph), 7.65 (1H, d, J=8.5 Hz, C$_7$—H)

(5) 1-acetyl-5-benzyloxycarbonylamino-8-methyl-2,3-dihydroquinolin-4(1H)-one:

In 20 ml of benzene 400 mg of the compound prepared in (4) above was dissolved. To this solution 0.28 ml of acetyl chloride and 0.34 ml of pyridine were added and the mixture was stirred at room temperature for 20 minutes. Then the mixture was heated under reflux for 1.5 hours. The reaction mixture was washed with water and saturated sodium chloride aqueous solution, dried over anhydrous sodium sulfate. The solvent was removed under reduced pressure to yield 446 mg of the title compound as colorless crystals.

NMR (CDCl$_3$) δ: 1.57 (3H, s, CH$_3$CO), 1.95 (3H, br. s, CH$_3$), 2.1–2.4 (2H, m, C$_3$—H), 2.5–3.6 (2H, m, C$_2$—H), 5.21 (2H, s, Ph—CH$_2$—), 7.25–7.5 (6H, m, Ph—H, C$_6$—H), 8.35 (1H, d, J=9.0 Hz, C$_7$—H)

(6) 1-acetyl-5-amino-8-methyl-2,3-dihydroquinolin-4(1H)-one (in formula II, Z=—N(Ac)—, m=0, n=2, $R_1$=H, $R_2$=8-Me):

In 30 ml of a mixed solvent of methanol and dioxane (2:1) 446 mg of the compound prepared in (5) above was dissolved. To this solution 2 drops of acetic acid, 2ml of water and 60 mg of 10% palladium on charcoal were added and the mixture was catalytically hydrogenated. The catalyst was removed by filtration and the filtrate was evaporated to dryness. The residue was purified with silica gel column chromatography using an ethyl acetate - hexane (1:1) mixture as an eluent. By the concentration of the fraction containing the title compound, 272 mg of the title compound was obtained as yellowish green crystals.

mp: 124°–125° C.

NMR (DMSO-$d_6$) δ: 1.97 (3H, s, $CH_3CO$), 2.41 (3H, s, $CH_3$), 2.5–3.0 (2H, m, $C_3$—H), 3.0–3.5 (1H, m, $C_2$—H), 4.8–5.2 (1H, m, $C_2$—H), 6.0–6.5 (2H, m, $NH_2$), 6.53 (1H, d, J=8.5 $H_z$, $C_6$—H), 7.14 (1H, d, J=8.5 $H_z$, $C_7$—H)

(7) 9-ethyl-1,2-dihydro-9-hydroxy-4-methyl-3H,12H-pyrano[3',4':6,7]indolizino[1,2-c]benzo[ij][2,7]-naphthilidine-10,13(9H,15H)-dione:

In 20 ml of toluene 123 mg of the compound prepared in (6) above and 134 mg of 7,8-dihydro-4-ethyl-4-hydroxy-1H-pyrano[3,4-f]indolizine-3,6,10(4H)-trione were added and the mixture was heated with stirring for 30 minutes using a Deanstark apparatus. To the reaction mixture was added 50 mg of p-toluene sulfonic acid and the mixture was heated under reflux with stirring for further 7 hours. After cooling, the crystalline product was collected by filtration and was thoroughly washed with ethyl acetate, ethanol, water, ethanol, and ether successively, and dried. To the yellowish coarse powder 10 ml of concentrated hydrochloric acid was added and the mixture was heated on a water bath for 1.5 hours. After cooling, 10% sodium hydroxide aqueous solution was added to the reaction mixture to adjust the pH to about 7. The deposited crystals were collected by filtration, and were thoroughly washed with water, ethanol, ethyl acetate, and ether successively, and dried to yield 50 mg of the title compound.

mp: above 300° C. (dec.)

NMR (DMSO-$d_6$) δ: 0.88 (3H, t, J=7.0 $H_z$, $CH_3CH_2$), 1.89 (2H, q, J=7.0 $H_z$, $CH_3CH_2$), 2.25 (3H, s, $CH_3$), 3.0–3.6 (4H, m, $C_1$—H & $C_2$—H), 5.17 (2H, s, $C_{15}$—H or $C_{12}$—H), 5.41 (2H, s, $C_{12}$—H or $C_{15}$—H), 6.00 (1H, br. s, NH), 6.43 (1H, s, OH), 7.26 (1H, d, J=9.0 $H_z$, $C_6$—H), 7.29 (1H, s, $C_8$—H), 7.45 (1H, d, J=9.0 $H_z$, $C_5$—H),

IR $v_{max}^{KBr}$ cm$^{-1}$: 3406, 1746, 1659, 1593, 1455

Elemental analysis for $C_{23}H_{21}N_3O_4 \cdot H_2O$:
Calculated: C 65.55; H 5.50; N 9.97;
Found: C 65.21; H 5.22; N 9.78.

EXAMPLE 5

Preparation of 4-chloro-9-ethyl-2,3-dihydro-9-hydroxy-1H,12H-benzo[de]pyrano[3',4':6,7]indolizino[1,2-b]-quinoline-10,13(9H,15H)-dione: (in formula IA, Z=—$CH_2$—, $R_1$=4-Cl, $R_2$=H, and $R_3$=Et)

(1) 5-chloro-3,4-dihydro-8-nitro-1(2H)-naphthalenone:

In 78 ml of concentrated sulfuric acid 13.08 g of 5-chloro-3,4-dihydro-1(2H)-naphthalenone was dissolved. To the solution was added a solution obtained by dissolving 8.82 g of potassium nitrate in 78 ml of concentrated sulfuric acid at 0° C., and the mixture was stirred for 1.5 hours. The reaction mixture was charged into 1 liter of water and extracted with dichloromethane. The organic layer was washed with water, saturated sodium bicarbonate aqueous solution, and saturated sodium chloride aqueous solution successively, and dried over anhydrous sodium sulfate. The solvent was evaporated and the residue was subjected to silica gel column chromatography. From the fraction using a mixed solvent of chloroform - n-hexane (1:3) as an eluent, 7.29 g of the title compound was obtained.

mp: 120°–121° C. (chloroform-n-hexane)

NMR (CDCl$_3$) δ: 2.0–2.5 (2H, m, $C_3$—H), 2.73 (2H, t, J=7.6 $H_z$, $C_2$—H), 3.07 (2H, t, J=6.0 $H_z$, $C_4$—H), 7.30 (1H, d, J=8.0 $H_z$, $C_6$—H), 7.64 (1H, d, J=8.0 $H_z$, $C_7$—H)

IR $v_{max}^{KBr}$ cm$^{-1}$: 1698, 1587, 1539

Elemental analysis for $C_{10}H_8NO_3Cl$:
Calculated: C 53.23; H 3.57; N 6.21;
Found: C 53.15; H 3.59; N 6.25.

(2) 8-amino-5-chloro-3,4-dihydro-1(2H)-naphthalenone: (in formula II, Z=—$CH_2$—, m=0, n=2, $R_1$=Cl, and $R_2$=H)

To a mixture of 15 ml ethanol and 7 ml dioxane and 3 g of Raney nickel was added 600 mg of the compound prepared in (1) above and the mixture was subjected to reduction in a hydrogen stream for 1.5 hours. Raney nickel was removed from the reaction mixture by filtration and the filtrate was evaporated to dryness to yield 479 mg of the title compound.

mp: 84°–86° C. (dichloromethane - n-hexane)

NMR (CDCl$_3$) δ: 2.05 (2H, tt, J=6.1, 6.4 $H_z$, $C_3$—H), 2.63 (2H, t, J=6.4 $H_z$, $C_2$—H), 2.95 (2H, t, J=6.1 $H_z$, $C_4$—H), 5.4 (2H, bs, $NH_2$), 6.45 (1H, d, J=8.5 $H_z$, $C_7$—H), 7.21 (1H, d, J=8.5 $H_z$, $C_6$—H)

IR $v_{max}^{KBr}$ cm$^{-1}$: 3454, 3340, 1644, 1608, 1455

Elemental analysis for $C_{10}H_{10}NOCl$:
Calculated: C 61.39; H 5.15; N 7.16;
Found: C 61.41; H 5.11; N 7.17.

(3) 4-chloro-9-ethyl-2,3-dihydro-9-hydroxy-1H,12H-benzo[de]pyrano[3',4':6,7]indolizino[1,2-b]quinoline-10,13(9H,15H)-dione:

To 60 ml of toluene were added 479 mg of the compound prepared in (2) above, 429 mg of 7,8-dihydro-4-ethyl-4-hydroxy-1H-pyrano[3,4-f]indolizine-3,6,10 (4H)-trione, and 251 mg of p-toluene sulfonic acid, and the mixture was heated under refluxed for 2 hours using Deanstark apparatus. The reaction mixture was cooled and filtered to collect deposited crystals were collected by filtration, which were thoroughly washed with ethyl acetate and dichloromethane successively, and were recrystallized from a mixed solvent of chloroform and methanol to yield 346 mg of the title compound.

mp: 258°–268° C. (dec.)

NMR (DMSO-$d_6$) δ: 0.89 (3H, t, J=7.2 $H_z$, $CH_3$), 1.88 (2H, q, J=7.2 $H_z$, $CH_3\underline{H}_2$), 1.8–2.4 (2H, m, $C_2$—H), 3.0–3.4 (4H, m, $C_1$—H, $C_3$—H), 5.27 (2H, s, $C_{15}$—H), 5.43 (2H, s, $C_{12}$—H), 6.47 (1H, s, OH), 7.33 (1H, s, $C_8$—H), 7.83 (1H, d, J=9.0 $H_z$, $C_6$—H), 7.99 (1H, d, J=9.0 $H_z$, $C_5$—H), IR $v_{max}^{KBr}$ cm$^{-1}$: 3484, 1743, 1662, 1611, Elemental analysis for $C_{23}H_{19}N_2O_4Cl$:
Calculated: C 65.33; H 4.53; N 6.62;
Found: C 65.49; H 4.60; N 6.60.

EXAMPLE 6

Preparation of
(S)-9-ethyl-2,3-dihydro-4,9-dihydroxy-1H,12H-benzo[de]pyrano[3',4':6,7]indolizino[1,2-b]-quinoline-10,13(9H,15H)-dione: (in formula IA, Z=—CH$_2$—, R$_1$=4-OH, R$_2$=H, and R$_3$=Et)

In 120 ml of acetic acid 1.44 g of 8-amino-3,4-dihydro-5-hydroxy-1(2H)-naphthalenone hydrochloride (in formula II, Z=—CH$_2$—, m=0, n=2, R$_1$=5-OH, R$_2$=H) and 1.94 g of (S)-7,8-dihydro-4-ethyl-4-hydroxy-1H-pyrano[3,4-f]indolizine-3,6,10(4H)-trione (in formula III, R$_3$=Et) were dissolved and the mixture was stirred at 100° C. for 11 hours. Following this, the same procedure was repeated as in Example 1 to obtain the title compound.

mp: 221°-226° C. (dec.) $[\alpha]_D^3$ = −23.0° C. (C =0.235, in DMSO)

NMR (DMSO-d$_6$) δ: 0.94 (3H, t, J=7 Hz, CH$_3$), 1.70–2.40 (4H, m, C$_2$—H & CH$_2$CH$_3$), 2.80–3.30 (4H, m, C$_2$—H & C$_3$—H), 5.20 (2H, s, CH$_2$—N), 5.46 (2H, s, CH$_2$—O), 7.29 (1H, s, C$_8$—H), 7.50 (1H, d, J=8.9 Hz, C$_5$—H), 7.86 (1H, d, J=8.9 Hz, C$_6$—H)

IR $\nu_{max}^{KBr}$ cm$^{-1}$ : 3428, 1740, 1658, 1592

Elemental analysis for C$_{23}$H$_{20}$N$_2$O$_5$.1/2H$_2$O:
Calculated: C 66.82; H 5.12; N 6.78;
Found : C 67.10; H 5.04; N 6.55.

EXAMPLE 7

Preparation of
8-ethyl-1,2-dihydro-8-hydroxy-3-methoxy-11H-cyclopenta[de]pyrano[3',4':6,7]indolizino[1,2-b]-quinoline-9,12(8H,14H)-dione: (in formula I, Z=—CH$_2$—, m=1, n=0, R$_1$=3-OMe, R$_2$=H)

To a mixture of 13 ml of methanol and 670 mg of 7-amino-4-methoxyindane-1-one (in formula II, Z=—CH$_2$—, m=1, n=0, R$_1$=4-OMe, R$_2$=H) was dissolved, and 2 ml of concentrated hydrochloric acid was added. After the solvent was evaporated to dryness, 860 mg of 4-ethyl-7,8-dihydro-4-hydroxy-1H-pyrano[3,4-f]indolizine-3,6,10(4H)-trione and 80 ml of acetic acid were added and to the residue and the residue was stirred at 100° C. for 9 hours. The precipitate was collected by filtration and washed thoroughly with chloroform and methanol to yield 90 mg of the title compound.

mp: above 300° C.

NMR (CF$_3$COOD) δ: 1.17 (3H, t, J=7 Hz, CH$_3$CH$_2$), 2.19 (2H, q, J=7 Hz, CH$_3$CH$_2$), 3.8–4.0 (4H, m, C$_1$—H, C$_2$—H), 4.24 (3H, s, CH$_3$O), 5.74 (2H, s, C$_{14}$—H), 5.66–5.97 (2H, ABq, J=18 Hz, C$_{11}$—H), 8.14 (1H, d, J=9 Hz, C$_4$—H), 8.31 (1H, d, J=9 Hz, C$_5$—H), 8.43 (1H, s, C$_7$—H)

Elemental analysis for C$_{23}$H$_{20}$N$_2$O$_5$.7/4H$_2$O
Calculated: C 63.37; H 5.43; N 6.43;
Found : C 63.62; H 5.14; N 6.13.

EXAMPLE 8

Preparation of
8-ethyl-1,2-dihydro-3,8-dihydroxy-11H-cyclopenta[de]-pyrano[3',4':6,7]indolizino[1,2-b]-quinoline-9,12(8H,14H)-dione: (in formula I, Z=—CH$_2$—, m=1, n=0, R$_1$=3-OH, R$_2$=H, R$_3$=Et)

To 2.28 g of 7-amino-4-methoxyindane-1-one 110 ml of 47% hydrobromic acid was added and the mixture was heated under reflux for 3.5 hours. The reaction mixture was charged into ice, the mixture was neutralized by adding sodium bicarbonate, and then extracted with ethyl acetate. The organic layer was washed with water and saturated sodium chloride aqueous solution, dried over anhydrous sodium sulfate. The solvent was evaporated to dryness to yield 2.10 g of 7-amino-4-hydroxyindane-1-one.

mp: 270° C. (dec.)

NMR (CDCl$_3$) δ: 2.5–2.7 (2H, m, C$_2$—H), 2.8–3.0 (2H, m, C$_3$—H), 6.43 (1H, d, J=8.5 Hz, C$_6$—H), 6.84 (1H, d, J=8.5 Hz, C$_5$—H)

To 280 ml of 1,2-dichloroethane were added 1.00 g of the compound obtained above, 1.61 g of 4-ethyl-7,8-dihydro-4-hydroxy-1H-pyrano[3,4-f]indolizine-3,6,10(4H)-trione, and 350 mg of p-toluene sulfonic acid, and the mixture was refluxed under heating for 30 minutes. To this was added 90 ml of ethanol, and the mixture was refluxed for 20.5 hours. 1.61 g of 4-ethyl-7,8-dihydro-4-hydroxy-1H-pyrano[3,4-f]indolizine-3,6,10(4H)-trione was added to the reaction mixture and refluxing under heating was conducted for further 13 hours. Precipitate produced was collected by filtration. To this was added 100 ml of chloroform, 80 ml of methanol, and 40 ml of 10% hydrochloric acid, and the mixture was refluxed for 1 hour. The insoluble material was collected by filtration and recrystallized from acetic acid to yield 375 mg of the title compound.

mp: 270° C. (dec.)

NMR (CF$_3$COOD) δ: 1.18 (3H, t, J=8 Hz, CH$_3$), 2.18 (2H, q, J=8 Hz, CH$_3$CH$_2$), 3.7–4.1 (4H, m, C$_1$—H, C$_2$—H), 5.75 (2H, s, C$_{14}$—H), 5.65, 5.98 (2H, ABq, J=17 Hz, C$_{11}$—H), 8.05 (1H, d, J=10 Hz, C$_4$—H), 8.15 (1H, d, J=10 Hz, C$_5$—H), 8.29 (1H, s, C$_7$—H)

IR $\nu_{max}^{KBr}$ cm$^{-1}$ : 3300, 1749, 1653, 1587, 1497

Elemental analysis for C$_{22}$H$_{18}$N$_2$O$_5$.3/4H$_2$O
Calculated: C 65.42; H 4.87; N 6.94;
Found : C 65.59; H 5.13; N 7.10.

EXAMPLE 9

Preparation of
8-ethyl-1,2-dihydro-3,8-dihydroxy-11H-cyclopenta[de]-pyrano[3',4':6,7]indolizino[1,2-b]-quinoline-9,12(8H,14H)-dione: (in formula I, Z=—CH$_2$—, m=1, n=0, R$_1$=3-OH, R$_2$=H, R$_3$=Et)

A mixture of 46 mg of the compound prepared in Example 7 and 2 ml of 47% hydrobromic acid was refluxed for 2 hours. The reaction mixture was charged into ice and the insoluble material was collected by filtration. This was washed with water, methanol, ethyl acetate, and chloroform successively, and was recrystallized from acetic acid to yield 22 mg of the title compound. The NMR spectrum of this compound was identical to that of the compound prepared in Example 8.

Elemental analysis for C$_{22}$H$_{18}$N$_2$O$_5$.5/4H$_2$O
Calculated: C 63.99; H 5.00; N 6.78;
Found : C 63.93; H 5.10; N 6.55.

EXAMPLE 10

Preparation of
9-ethyl-1,2-dihydro-9-hydroxy-4-methoxy-12H-pyrano[4,3,2-de]pyrano[3',4':6,7]indolizino[1,2-b]-quinoline-10,13(9H,15H)-dione: (in formula IA, Z=—O—, R$_1$=4-OMe, R$_2$=H, R$_3$ =Et)

(1) 3-(3-acetylamino-6-methoxyphenoxy)propionic acid:

To 50 ml of water 3.26 g of potassium hydroxide was dissolved, and then 50 ml of dioxane was added. To this solution 9 g of N-(3-hydroxy-4-methoxyphenyl)acetamide and then 100 mg of 18-crown-6 were added. To the mixture was added 4 g of β-propiolactone with stirring at room temperature. The mixture was stirred overnight. To this was added 100 ml of water and the mixture was washed three times with ethyl acetate. The aqueous layer was acidified with 10% hydrochloric acid and extracted three times with ethyl acetate. The extract was washed with water and dried over anhydrous sodium sulfate. The solvent was evaporated to dryness to yield a light brown powder. This powder was recrystallized from acetic acid to yield 2.8 g of the title compound as a colorless powder.

mp: 157°–158° C.

NMR (DMSO-$d_6$) δ: 1.99 (3H, s, $CH_3$), 2.69 (2H, t, J=7 $H_z$, $OCH_2$), 3.70 (3H, s, $OCH_3$), 4.10 (2H, t, J=7 $H_z$, $CH_2$), 6.85 (1H, d, J=9 $H_z$, Ar), 7.08 (1H, dd, J=9 and 3 $H_z$, Ar), 7.29 (1H, d, J=3 $H_z$, Ar)

(2) 5-amino-8-methoxy-4-chromanone:

In 20 ml of 6 N hydrochloric acid 1 g of the compound prepared in (1) above was dissolved and the mixture was heated under reflux for 1 hour. The solvent was evaporated to dryness to yield 960 mg of a light brown powder, which was dissolved in 10 ml of sulfuric acid. The mixture was stirred at 50° C. under nitrogen gas stream for 1 hour. The mixture added into ice water, was made alkaline with sodium carbonate, extracted with ethyl acetate, and the extract was washed with water, and dried over sodium sulfate. The solvent was removed to yield 190 mg of the title compound.

mp: 124°–125° C.

NMR ($CDCl_3$) δ: 2.79 (2H, t, J=7 $H_z$, $C_3$—H), 3.80 (3H, s, Me), 4.52 (2H, t, J=7 $H_z$, $C_2$—H), 6.16 (1H, d, J=9 $H_z$, $C_6$—H), 6.96 (1H, d, J=9 $H_z$, $C_7$—H)

(3) 9-ethyl-1,2-dihydro-9-hydroxy-4-methoxy-12H-pyrano[4,3,2-de]pyrano[3',4':6,7]indolizino[1,2-b]-quinoline-10,13(9H,15H)-dione:

To 20 ml of acetic acid 410 mg of the compound prepared in (2) above and 560 mg of 4-ethyl-7,8-dihydro-4-hydroxy-1H-pyrano[3,4-f]indolizine-3,6,10(4H)-trione were added, and the mixture was refluxed under nitrogen stream for 5 hours. After cooling, the precipitate was collected by filtration, washed with acetone, and recrystallized from acetic acid to yield 590 mg of the title compound.

mp: 273°–276° C. (dec.)

NMR (DMSO-$d_6$) δ: 3.96 (3H, s, Me), 5.25 (2H, s, $C_{12}$13 H or $C_{15}$—H), 5.43 (2H, s, $C_{12}$—H or $C_{15}$—H), 6.46 (1H, s, OH), 7.30 (1H, s, $C_8$—H), 7.76 (2H, s, $C_5$ & $C_6$—H)

IR $\nu_{max}^{KBr}$ $cm^{-1}$: 3406, 3094, 1743, 1662, 1608

Elemental analysis for $C_{23}H_{20}N_2O_6$:
Calculated: C 65.71; H 4.80; N 6.66;
Found : C 65.18; H 4.80; N 6.48.

EXAMPLE 11

Preparation of 9-ethyl-1,2-dihydro-4,9-dihydroxy-12H-pyrano[4,3,2-de]pyrano[3',4':6,7]indolizino[1,2-b]-quinoline-10,13(9H,15H)-dione: (in formula IA, Z=—O—, $R_1$=4-OH, $R_2$=H, $R_3$=Et)

A mixture of 412 mg of the compound prepared in Example 10 and 10 ml of 47% hydrobromic acid was refluxed under nitrogen stream for 1 hour under heating. The reaction mixture was charged into ice water and centrifuged to collect the precipitate. The precipitate was washed with water and acetone, and recrystallized from a mixture of chloroform - methanol to yield 390 mg of the title compound.

mp: 273°–274° C. (dec.)

NMR (DMSO-$d_6$) δ: 0.90 (3H, t, J=7 $H_z$, $CH_3$), 1.88 (2H, q, J=7 $H_z$, $CH_3\underline{CH_2}$), 5.23 (2H, s, $C_{12}$—H or $C_{15}$—H), 5.42 (2H, s, $C_{12}$—H or $C_{15}$—H), 6.42 (1H, br. s, OH), 7.29 (1H, s, $C_8$—H), 7.47 (J=1H, d, J=9 $H_z$, $C_5$—H), 7.64 (1H, d, J=9 $H_z$, $C_6$—H)

IR $\nu_{max}^{KBr}$ $cm^{-1}$: 3400, 3106, 1755, 1656, 1584

Elemental analysis for $C_{22}H_{18}N_2O_5 \cdot 1/2H_2O$:
Calculated: C 63.61; H 4.61; N 6.74;
Found : C 63.81; H 4.78; N 6.72.

Example 12

Preparation of 4-[2-(dimethylamino)ethoxy]-9-ethyl-2,3-dihydro-9-hydroxy-1H,12H-benzo[de]pyrano[3',4':6,7]-indolizino[1,2-b]quinoline-10,13(9H,15H)-dione: (in formula IA, Z=—$CH_2$—, $R_1$=4-$Me_2NCH_2CH_2O$, $R_2$=H, $R_3$=Et)

(1) 5-[2-(dimethylamino)ethoxy]-3,4-dihydro-8-nitro-1(2H)-naphthalenone:

A mixture of 25 ml of dimethylformamide, 1.39 g of 3,4-dihydro-5-hydroxy-8-nitro-1(2H)-naphthalenone and 9.38 g of potassium carbonate was stirred at 90° C. for 15 minutes. To the reaction mixture 3.09 g of 2-(dimethylamino)ethylchloride was added and the mixture was stirred at the same temperature for further 30 minutes. The solvent was evaporated to dryness, and the residue was purified by silica gel column chromatography using a mixture of chloroform - methanol (100:2) as an eluent to yield 1.26 g of the title compound as an oily substance.

NMR ($CDCl_3$) δ: 1.95–2.35 (2H, m, $C_3$—H), 2.37 (6H, s, $CH_3$), 2.70 (2H, t, J=6.1 $H_z$, $C_2$13 H or $C_4$—H), 2.81 (2H, t, J=5.5 $H_z$, N—$CH_2$), 2.92 (2H, t, J=6.1 $H_z$, $C_4$—H or $C_2$—H), 4.15 (2H, t, J=5.5 $H_z$, O—$CH_2$), 6.98 (1H, d, J=8.7 $H_z$, $C_6$—H), 7.37 (1H, d, J=8.7 $H_z$, $C_7$—H)

(2) 8-amino-5-[2-(dimethylamino)ethoxy]-3,4-dihydro-1(2H)-naphthalenone-hydrochloride:

The compound prepared in (1) above weighing 1.10 g was dissolved in 25 ml of ethanol. To the solution 88 mg of platinic oxide was added and the mixture was shaken under hydrogen atmosphere. The reduction was ceased when 265 ml of hydrogen was absorbed. To the mixture was added 3 ml of concentrated hydrogen chloride, and the insoluble material was removed by filtration. The solvent was removed to yield 1.34 g of the title compound.

mp: 150°–160° C. (dec.)

NMR ($CD_3OD$) δ: 1.9–2.4 (2H, m, $C_3$—H), 2.75 (2H, t, J=6.4 $H_z$, $C_2$—H or $C_4$—H), 3.06 (6H, s, Me), 3.03–3.3 (2H, m, $C_4$—H or $C_2$—H), 3.75 (2H, t, J=5.5 $H_z$, N=$CH_2$), 4,54 (2H, t, J=5.5 $H_z$, O—$CH_2$), 7.43 (2H, s, $C_6$—H, $C_7$—H)

(3) 4-[2-(dimethylamino)-ethoxy]-9-ethyl-2,3-dihydro-9-hydroxy-1H,12H-benzo[de]pyrano[3',4':6,7]-indolizino[1,2-b]quinoline-10,13(9H,15H)-dione:

To 50 ml of acetic acid 705 mg of the compound prepared in (2) above and 579 mg of 4-ethyl-7,8-dihydro-4-hydroxy-1H-pyrano[3,4-f]indolizine-3,6,10(4H)-trione were added and the mixture was refluxed for 6 hours. The precipitate was collected by filtration and recrystallized from methanol to yield 359 mg of the title compound.

mp: 215°–230° C. (dec.)

NMR (DMSO-d$_6$) δ: 0.89 (3H, t, J=7.1 Hz, C$\underline{H_3}$CH$_2$), 1.88 (2H, q, J=7.1 Hz, CH$_3$C$\underline{H_2}$), 1.80–2.25 (2H, m, C$_2$—H), 2.91 (6H, d, J=5.0 Hz, N—CH$_3$), 2.80–3.30 (4H, m, C$_1$—H, C$_3$—H), 3.65–3.80 (2H, m, N—C$\underline{H_2}$CH$_2$), 4.59 (2H, t, J=4.4 Hz, O—CH$_2$C$\underline{H_2}$), 5.19 (2H, s, C$_{15}$—H), 7.32 (1H, s, C$_8$—H), 7.74 (1H, d, J=9.5 Hz, C$_5$—H), 8.03 (1H, d, J=9.5 Hz, C$_6$—H)

IR $\nu_{max}^{KBr}$ cm$^{-1}$: 3300, 2224, 1920, 1740, 1704, 1653, 1614

Elemental analysis for C$_{27}$H$_{29}$N$_3$O$_5$.2HCl.1/2H$_2$O:
Calculated: C 58.17; H 5.79; N 7.54; Cl 12.72;
Found: C 58.22; H 5.87; N 7.39; Cl 12.64.

EXAMPLE 13

Preparation of 9-ethyl-1,2-dihydro-4-(3-dimethylamino)-propylamino-9-hydroxy-12H-thiino[4,3,2-de]pyrano[3',4':6,7]-indolizino [1,2-b]quinoline-10,13(9H,15H)-dione. dihydrochloride: (in formula IA, Z=—S—, R$_1$=Me$_2$NCH$_2$CH$_2$CH$_2$NH, R$_2$=H, R$_3$=Et)

(1) 5-acetylamino-8-amino-4-thiochromanone:

To a solution of 23.2 g of 5-acetylamino-8-nitro-4thiochromanone in 1 liter of acetic acid was added 5 gm of 10% palladium on charcoal, and the mixture was catalytically hydrogenated. After removing the catalyst by filtration, the solvent was evaporated and hexane was added to the residue. The precipitate was filtered to yield 19.4 gm of the title compound.

$^1$H-NMR (CDCl$_3$) δ: 2.19 (3H, s, NHCOCH$_3$), 2.8–3.4 (4H, C$_2$—H & C$_3$—H), 6.88 (1H, d, J=9.0 Hz, C$_7$—H), 8.34 (1H, d, J=9.0 Hz, C$_6$—H), (2) 5-acetylamino-8-dimethylaminopropylamino-4-thiochromanone:

A mixture of 446 mg of 5-acetylamino-8-amino-4-thiochromanone and 620 mg of 3-(dimethylamino)propylchloride. hydrochloride was heated at 145° C. for 15 minutes. After cooling, 10% sodium hydroxide aqueous solution was added to the mixture, which was then extracted three times with dichloromethane. The dichloromethane layer was washed with saturated sodium chloride aqueous solution and dried. The solvent was evaporated to dryness and residue was purified with silica gel column chromatography using a mixture of chloroform - methanol (20:1) as an eluent. The solvent was evaporated from the fraction containing the title compound, 225 mg of which was obtained as a yellow oily substance.

NMR (CDCl$_3$) δ: 1.6–2.0 (2H, m, NHCH$_2$C$\underline{H_2}$CH$_2$N), 2.18 (3H, s, NHCOC$\underline{H_3}$), 2.28 (6H, s, NMe$_2$), 2.45 (2H, t, J=6.6 Hz, NHCH$_2$CH$_2$C$\underline{H_2}$N), 2.7–3.4 (6H, m, NHCH$_2$CH$_2$CH$_2$N, C$_2$—H & C$_3$—H), 6.79 (1H, d, J=9.0 Hz, C$_7$—H), 8.37 (1H, d, J=9.0 Hz, C$_6$—H), (3) 9-ethyl-1,2-dihydro-4-(3-dimethylamino)-propylamino-9-hydroxy-12H-thiino[4,3,2-de]-pyrano[3',4':6,7]-indolizino [1,2-b]quinoline-10,13(9H,15H)-dione.dihydrochloride:

A mixture of 225 g of the compound prepared in (2) above and 5 ml of concentrated hydrochloric acid was heated at 70°–80° C. for 3 hours. After cooling, the mixture was made weakly alkaline with 10% sodium hydroxide aqueous solution. The mixture was extracted with dichloromethane three times, and the extract was washed with saturated sodium chloride aqueous solution and dried over anhydrous sodium sulfate. The solvent was evaporated to dryness and to the residue were added 5 ml of methanol and 1 ml of concentrated hydrochloric acid. Then, the solvent was evaporated to dryness. This procedure was repeated four times. To the residue thus obtained 167 mg of 7,8-dihydro-4-ethyl-4-hydroxy-1H-pyrano[3,4-f]indolizine-3,6,10(4H)trione and 10 ml of acetic acid were added, and the mixture was refluxed for 6 hours. After cooling, the precipitate was collected by filtration, and was washed with ethyl acetate, chloroform, and then with ether, and finally dried to yield a red-brown powder. This powder was purified by means of high performance liquid chromatography [column: nucleocil C$_{18}$ (manufactured by Nagel Co.); eluent: methanol and water (7:3, the pH was adjusted to 3 with hydrochloric acid)]to yield 62 mg of the title compound in a form of red-purple crystals.

mp: 265°–270° C.

NMR (D$_2$O) δ: 1.04 (3H, t, J=7.0 Hz, CH$_2$C$\underline{H_3}$), 1.9–2.3 (4H, m, C$\underline{H_2}$CH$_3$ and NHCH$_2$C$\underline{H_2}$CH$_2$NMe$_2$), 3.02 (6H, s, NMe$_2$), 2.9–3.5 (8H, m, C$_2$—H, C$_3$—H, and NHC$\underline{H_2}$CH$_2$C$\underline{H_2}$NMe$_2$), 4.06 (1H, d, J=20 Hz, C$_{12}$—H), 4.21 (1H, d, J=20 Hz, C$_{12}$—H), 5.42 (2H, br. s, C$_{15}$—H), 7.13 (1H, d, J=9.0 Hz, C$_5$—H), 7.16 (1H, s, C$_8$—H), 7.44 (1H, d, J=9.0 Hz, C$_6$—H)

IR $\nu_{max}^{KBr}$ cm$^{-1}$: 1746, 1653, 1608, 1533, 1416, 1161

Elemental analysis for C$_{27}$H$_{30}$N$_4$O$_4$S.2HCl.H$_2$O
Calculated: C 54.27; H 5.73; N 9.38;
Found : C 54.71; H 5.63; N 9.52.

EXAMPLE 14

Preparation of 9-ethyl-2,3-dihydro-9-hydroxy-4-methoxy-1H,12H-benzo[de]pyrano[3',4':6,7]indolizino[1,2-b]quinoline-10,13(9H,15H)-dione: (in formula IA, Z=—CH$_2$—, R$_1$=4-OMe, R$_2$=H, R$_3$=Et)

(1) 8-nitro-3,4-dihydro-5-methoxy-1(2H)-naphthalenone:

In 5 ml of N,N-dimethylformamide 415 mg of 8-nitro-3,4-dihydro-5-hydroxy-1(2H)-naphthalenone was dissolved. To this was added 88 mg of 60% sodium hydride and the mixture was stirred for 5 minutes. To this was added 0.38 ml of methyl iodide and stirring was continued for further 1 hour. The reaction mixture was charged into ice water, and the whole was extracted with ethyl acetate. The extract was washed with water and dried over anhydrous sodium sulfate to condensate. The solvent was evaporated to dryness. To the residue was added a mixed solvent of ether and n-hexane, and deposited crystals were collected by filtration to yield 385 mg of the title compound.

mp: 90°–100° C. (dec.)

NMR (CDCl$_3$) δ: 1.8–2.4 (2H, m, C$_3$—H), 2.4–3.1 (4H, m, C$_2$—H, C$_4$—H), 3.92 (3H, s, OCH$_3$), 6.95 (1H, d, J=9.0 Hz, C$_6$—H), 7.42 (1H, d, J=9.0 Hz, C$_7$—H)

Elemental analysis for C$_{11}$H$_{11}$NO$_4$:
Calculated: C 59.72; H 5.01; N 6.33;
Found: C 59.82; H 5.09; N 6.27.

(2) 8-amino-3,4-dihydro-5-methoxy-1(2H)-naphthalenone. hydrochloride:

In 20 ml of a mixed solvent of ethanol and dioxane (1:1), 320 mg of the compound prepared in (1) above was dissolved. To this solution 5 drops of acetic acid and 50 mg of platinic oxide were added and the mixture was catalytically hydrogenated. The catalyst was removed by filtration. To the filtrate was added 1.6 ml of 1 N hydrochloric acid. The solvent was evaporated to dryness and to the residue was added ether. The precipitate was collected by filtration to yield 273 mg of the title compound.

mp: 165°–175 ° C. (dec.)

NMR (D$_2$O) δ: 1.8–2.4 (2H, m, C$_3$—H), 2.4–3.2 (4H, m, C$_2$—H, C$_4$—H), 3.91 (3H, s, OCH$_3$), 7.29 (2H, s, C$_6$—H, C$_7$—H)

Elemental analysis for C$_{11}$H$_{13}$NO$_2$.HCl.1/4H$_2$O:
Calculated: C 56.90; H 6.31; N 6.03;
Found : C 56.94; H 6.29; N 6.08.

(3) 9-ethyl-2,3-dihydro-9-hydroxy-4-methoxy-1H,12H-benzo[de]pyrano[3,,4,:6,7]indolizino[1,2-b]quinoline-10,13(9H,15H)-dione In 25 ml of acetic acid 500 mg of the compound prepared in (2) above and 530 mg of 7,8-dihydro-4-ethyl-4-hydroxy-1H-pyrano[3,4:f]indolizine-3,6,10(4H)-trione were dissolved and the mixture was stirred at 100 ° C. for 15 hours. After cooling, the precipitate was collected by filtration, and washed with chloroform and ether successively. 550 mg of the title compound was obtained.

mp: 265°–270 ° C. (dec.)

NMR (DMSO-d$_6$) δ: 0.89 (3H, t, J=7.0 Hz, CH$_3$), 1.7–2.2 (4H, m, C$_2$—H, CH$_3$CH$_2$), 2.9–3.3 (4H, m, C$_1$—H, C$_3$—H), 3.99 (3H, s, OCH$_3$), 5.25 (2H, s, C$_{15}$—H), 5.47 (2H, s, C$_{12}$—H), 7.32 (1H, s, C$_8$—H), 7.77 (1H, d, J=9.0 Hz, C$_5$—H), 8.08 (1H, d, J=9.0 H, C$_6$—H)

IR ν$_{max}^{KBr}$ cm$^{-1}$: 1746, 1659, 1608

Elemental analysis for C$_{24}$H$_{22}$N$_2$O$_5$.1/4H$_2$O:
Calculated: C 68.15; H 5.36; N 6.62;
Found : C 67.92; H 5.29; N 6.69.

EXAMPLE 15

Preparation of 4-(2-diethylamino)ethylamino-1,2-dihydro-9-ethyl-9-hydroxy-12H-thiino[4,3,2,-de]pyrano-[3',4':6,7]indolizino[1,2-b]quinoline-10,13(9H,15H)-dione. dihydrochloride: (in formula IA, Z=—S—, R$_1$=Et$_2$NCH$_2$CH$_2$NH, R$_2$=H, R$_3$=Et)

(1) 5-acetylamino-8-(2-diethylamino)ethylamino-4-thiochromone:

In 5 ml of dimethylacetamide 227 mg of 5-acetylamino-8-amino-4-thiochromone and 540 mg of 2-(diethylamino)-ethylchloride hydrochloride were dissolved. To the solution 210 mg of potassium carbonate was added and the mixture was stirred at 145° C. for 10 hours. The reaction mixture was charged into water, made alkaline with 10% sodium hydroxide aqueous solution, and extracted with ethyl acetate. The extract was washed with water and dried over anhydrous sodium sulfate. The solvent was evaporated to dryness, and the residue was purified with silica gel column chromatography using a mixed solvent of chloroform and methanol (20:1) as an eluent. Upon condensation of the fractions containing the title compound, 125 mg of the above title compound was obtained as a red-brown oil.

NMR (CDCl$_3$) δ: 1.10 (6H, t, J=7.0 Hz, N(CH$_2$CH$_3$)$_2$), 2.25 (3H, s, NHCOCH$_3$), 2.4–3.3 (8H, m, NHCH$_2$CH$_2$N(CH$_2$CH$_3$)$_2$), 6.97 (1H, d, J=10.0 Hz, C$_3$—H), 6.98 (1H, d, J=9.0 Hz, C$_7$—H), 7.86 (1H, d, J=10.0 Hz, C$_2$—H), 8.80 (1H, d, J=9.0 Hz, C$_6$—H)

(2) 5-acetylamino-8-(2-diethylamino)ethylamino-4-thiochromanone:

In 10 ml of acetic acid was dissolved 125 mg of 5-acetylamino-8-(2-diethylamino)ethylamino-4-thiochromone. To this solution 120 mg of 10% palladium-carbon was added and the solution was catalytically hydrogenated. The catalyst was removed by filtration, and the filtrate was evaporated to dryness. The residue was purified with silica gel column chromatography using a mixed of chloroform and methanol (20:1) as an eluent. Upon condensation of the fractions containing the target compound, 83 mg of the title compound was obtained as a red-brown oil.

NMR (CDCl$_3$) δ: 1.14 (6H, t, J=7.0 Hz, N(CH$_2$CH$_3$)$_2$), 2.19 (3H, s, NHCOCH$_3$), 2.78 (4H, q, J=7.0 Hz, N(CH$_2$CH$_3$)$_x$), 2.5–3.5 (8H, m, C$_2$—H, C$_3$—H, and NHCH$_2$CH$_2$N), 6.79 (1H, d, J=9.0 Hz, C$_6$—H, or C$_7$—H), 8.36 (1H, d, J=9.0 Hz, C$_7$—H, or C$_8$—H)

(3) 4-(2-diethylamino)ethyl-1,2-dihydro-9-ethyl-9-hydroxy-12H-thiino[4,3,2,-de]pyrano [3',4':6,7]indolizino-[1,2-b]quinoline-10,13(9H,15H)-dione.dihydrochloride:

In 2 ml of concentrated hydrochloric acid 80 mg of 5-acetylamino-8-(2-diethylamino)ethyl-4-thiochromanone was dissolved and the mixture was stirred at 80° C. for 3 hours. After cooling, the mixture was alkalinized with 10% sodium hydroxide aqueous solution and extracted three times with dichloromethane. The extract was washed with saturated sodium chloride aqueous solution and dried over anhydrous sodium sulfate. The solvent was evaporated to dryness and to the residue methanol and 1 ml of concentrated hydrochloric acid were added, and the solvent was evaporated to dryness. This addition and removal of the solvent and hydrochloric acid were repeated four times. To the residue which was finally obtained 34 mg of 7,8-dihydro-4-ethyl-4-hydroxy-1H-pyrano[3,4-f]indolizine-3,6,10(4H)trione and 3 ml of acetic acid were added and refluxed for 7 hours. The reaction mixture was condensed to the volume of about 1 ml. To the condensate ethyl acetate was added and the precipitate was to collected by filtration, which was thoroughly washed with ethyl acetate, chloroform, and then with ether, and dried to yield a red-brown powder. This substance was purified by means of high performance liquid chromatography (column: nucleocil C$_{18}$; eluent: a mixed solvent of methanol/water (7/3) which was adjusted to PH 3 with hydrochloric acid) to yield 39 m of the title compound as red-purple crystals.

mp: 215°–220° C.

NMR (DMSO-d$_6$) δ: 0.88 (3H, t, J=7.0 Hz, CH$_3$CH$_3$), 1.25 (6H, t, J=7.0 Hz, N(CH$_2$CH$_3$)$_2$), 1.88 (2H, q, J=7.0 Hz, H$_2$CH$_3$), 3.1–3.4 (8H, m, NHCH$_2$CH$_2$N(CH$_2$CH$_3$)$_2$), 3.47 (2H, m, C$_1$—H), 3.81 (2H, m, C$_2$—H), 5.28 (2H, s, C$_{14}$—H), 5.46 (2H, s, C$_{12}$—H), 7.27 (1H, s, C$_8$—H), 7.59 (1H, d, J=10.0 Hz, C$_5$—H), 7.91 (1H, d, J=10.0 , C$_6$—H)

IR ν$_{max}^{KBr}$ cm$^{-1}$: 1743, 1653, 1614, 1533, 1419, 1296

Elemental analysis for C$_{28}$H$_{32}$N$_4$O$_4$S.2HCl.3/2H$_2$O:
Calculated: C 54.19; H 6.01; N 9.03;
Found : C 54.24; H 5.91; N 9.04.

EXAMPLE 16

Preparation of 4-cyano-1,2-dihydro-9-ethyl-9-hydroxy-12H-thiino[4,3,2,-de]pyrano[3',4':6,7]indolizino[1,2-b]-quinoline-10,13(9H,15H)-dione: (in formula IA, Z=—S—, R$_1$=4-CN, R$_2$=H, R$_3$=Et)

(1) 5-acetylamino-8-cyano-4-thiochromanone:

In 1.762 mg of 5-acetylamino-8-amino-4-thiochromanone 28% hydrochloric acid and 7.5 g of ice were added. To the mixture 2 ml of an aqueous solution containing 0.552 g of sodium nitrite was added dropwise while maintaining the inner temperature at 0° C. The mixture was stirred at the temperature for 40 minutes and neutralized with sodium bicarbonate to prepare an aqueous solution of the diazonium salt.

In 7.5 ml of water 1.90 g of cuprous chloride was suspended. To this suspension 6.5 ml of an aqueous solution containing 3.19 g of potassium cyanide was added, stirred on an ice bath for 1 hour, and was further added 13 ml of ethyl acetate, by which two phases were formed. The above aqueous solution of diazonium salt was then added to the two-layer mixture, and was stirred vigorously at 0° C. for 30 minutes, then at room temperature for 30 minutes, and 80° C. for 30 minutes. Chloroform was added to the reaction mixture, which was shaken vigorously. Insoluble material was removed by filtration and the chloroform layer was separated. The aqueous layer was further extracted twice with chloroform. The combined chloroform layer was washed with water and saturated sodium bicarbonate aqueous solution, and dried, followed by evaporation of the solvent. The residue was subjected to silica gel column chromatography, and chloroform fractions containing the title compound was concentrated. To the residue was added hexane. The precipitate was collected by filtration and dried to yield 980 mg of the title compound.

mp: 192°–196° C.

NMR (CDCl$_3$) δ: 2.26 (3H, s, CH$_3$), 3.0–3.5 (4H, m, C$_2$—H and C$_3$—H), 7.63 (1H, d, J=9.0 H$_z$, C$_6$—H or C$_7$—H), 8.62 (1H, d, J=9.0 H$_z$, C$_7$—H or C$_6$—H)

IR $\nu_{max}^{KBr}$ cm$^{-1}$: 3136, 2218, 1704, 1644

(2) 5-amino-8-cyano-4-thiochromanone:

In 6 ml of concentrated hydrochloric acid 202 mg of the compound prepared in (1) above was dissolved, and the solution was heated at 80°–90° C. for 4 hours. After cooling, the mixture was made alkaline with 10% sodium hydroxide aqueous solution. The mixture was extracted four times with chloroform, and the extract was washed with water and saturated sodium chloride aqueous solution, and dried over anhydrous sodium sulfate, followed by evaporation of the solvent. The residue was subjected to silica gel column chromatography using chloroform as an eluent, and fractions containing the title compound was concentrated. Through the addition of hexane to the residue. Yellow crystals were collected by filtration to yield 155 mg of the title compound.

NMR (CDCl$_3$) δ: 2.9–3.4 (4H, m, C$_2$—H and C$_3$—H), 6.36 (1H, d, J=8.5 H$_z$, C$_6$—H), 7.31 (1H, d, J=8.5 H$_z$, C$_7$—H)

IR $\nu_{max}^{KBr}$ cm$^{-1}$: 3430, 3310, 2206, 1629, 1605

(3) 4-cyano-1,2-dihydro-9-ethyl-9-hydroxy-12H-thiino[4,3,2-de]-pyrano[3′,4′:6,7]indolizino[1,2-b]quinoline-10,13(9H,15H)-dione:

In 50 ml of toluene were added 83 mg of the compound prepared in (2) above and 117 mg of 4-ethyl-7,8-dihydro-4-hydroxy-1H-pyrano[3,4-f]indolizine-3,6,10(4H)-trione. This mixture was heated with stirring in a Deanstark apparatus for 30 minutes, a small amount of p-toluenesulfonic acid was added to the mixture and the refluxing was continued for seven hours. The reaction mixture was then cooled to collect deposited crystals by filtration, which was thoroughly washed with chloroform, ethyl acetate, methanol, and ether successively, followed by drying to yield 137 mg of the title compound as a yellow powder.

mp: above 300° C. (dec.)

NMR (DMSO-d$_6$) δ: 0.92 (3H, t, J=7.0 H$_z$, CH$_3$CH$_2$), 1.90 (2H, q, J=7.0 H$_z$, CH$_3$CH$_2$), 3.2–3.8 (4H, m, C$_1$—H and C$_2$—H), 5.37 (2H, br. s, C$_{12}$—H), 5.46 (2H, br. s, C$_{15}$—H), 7.36 (1H, s, C$_{11}$—H), 7.97 (2H, s, C$_5$—H, and C$_6$—H)

IR $\nu_{max}^{KBr}$ cm$^{-1}$: 3400, 2944, 2224, 1747, 1662, 1611

Elemental analysis for C$_{27}$H$_{17}$N$_3$O$_4$S:

Calculated: C 64.03; H 3.97; N 9.74;

Found: C 63.95; H 4.05; N 9.55.

EXAMPLE 17

Preparation of 4-acetylaminomethyl-1,2-dihydro-9-ethyl-9-hydroxy-12H-thiino[4,3,2,-de]pyrano[3′,4′:6,7]-indolizino[1,2-b]quinoline-10,13(9H,15H)-dione: (in formula IA, Z=—S—, R$_1$=4-CH$_2$NHAc, R$_2$=H, R$_3$=Et)

(1) 5-acetylamino-8-aminomethyl-4-thiochromanone:

The compound prepared in Example 16 (1) weighing 980 mg was dissolved in 30 ml of acetic acid, and to this solution was added 900 mg of 10% palladium - carbon to effect catalytic hydrogenation. The catalyst was removed by filtration and the solvent of the filtrate was evaporated to dryness. To the residue 15 ml of concentrated hydrochloric acid was added and the mixture was stirred at 80° C. for 4 hours. After condensing the reaction mixture to dryness, a small amount of water was added to the residue, which was then made weakly alkaline with 10% sodium hydroxide aqueous solution. The mixture was extracted 4 times with a 10% methanolic chloroform. The extract was dried over anhydrous sodium sulfate, and the solvent was evaporated to dryness. To the residue was added n-hexane and the yellow crystals were collected by filtration to yield 500 mg of the title compound.

mp: above 106°–110° C.

NMR (CDCl$_3$) δ: 2.8–3.3 (4H, m, C$_2$—H and C$_3$—H), 3.75 (2H, s, —CH$_2$NH$_2$), 6.36 (1H, d, J=8.3 H$_z$, C$_6$—H or C$_7$—H), 6.3–7.0 (2H, m, NH$_2$), 7.12 (1H, d, J=8.3 H$_z$, C$_7$—H or C$_6$—H)

IR $\nu_{max}^{KBr}$ cm$^{-1}$: 3400, 3352, 3280, 1608

(2) 8-acetylaminomethyl-5-amino-4-thiochromanone:

The compound prepared in (1) above weighing 117 mg was dissolved in 8 ml of a 1% pyridine - toluene mixed solvent. To this solution 1 ml of 8.8% acetic acid anhydride-toluene was added gradually while stirring under ice cooling. After continued stirring for 30 minutes at room temperature, the solvent was distilled off from the reaction mixture and chloroform was added. This mixture was washed with water and saturated sodium chloride aqueous solution, dried over anhydrous sodium sulfate. The solvent was evaporated to dryness and to the residue a small amount of ethyl acetate and then hexane was added. Pale yellow crystals were collected by filtration to yield 178 mg of the title compound.

NMR (CDCl$_3$)δ: 1.99 (3H, s, COCH$_3$), 2.8–3.3 (4H, m, C$_2$—H and C$_4$—H), 4.35 (2H, d, J=4.6 H$_z$, CH$_2$NHCOCH$_3$), 6.36 (1H, d, J=8.5 Hz, C$_6$—H), 6.45–6.80 (1H, m, NHCOCH$_3$), 7.17 (1H, d, J=8.5 H$_z$, C$_7$—H), IR $\nu_{max}^{KBR}$ cm$^{-1}$: 3423, 3298, 2914, 1623, 1605, 1557

(3) 4-acetylaminomethyl-1,2-dihydro-9-ethyl-9-hydroxy-12H-thiino[4,3,2,-de]pyrano[3′,4′: 6,7]indolizino[1,2-b]-quinoline-10,13(9H,15H)-dione:

In 30 ml of acetic acid were dissolved 746 mg of the compound prepared in (2) above, 780 mg of 4-ethyl-7,8-dihydro-4-hydroxy-1H-pyrano[3,4-f]indolizine-3,6,10(4H)-trione, and a small amount of p-toluenesulfonic acid, and the mixture was stirred at 100°–110° C. for 3 hours. The solvent was evaporated to dryness, ethyl acetate was added to the residue, and crystals deposited were collected by filtration, washed thoroughly with ethyl acetate, chloroform, ethanol, and ether successively, and dried to yield 360 mg of the title compound as a yellow powder.

mp: 267°–271° C. (dec.)

NMR (DMSO-$d_6$) δ: 0.90 (3H, t, J=7.0 Hz, $\underline{CH_3}CH_2$), 1.88 (2H, q, J=7.0 Hz, $CH_3\underline{CH_2}$), 1.95 (3H, s, $COCH_3$), 3.2–3.6 (4H, m, $C_1$—H and $C_2$—H), 4.04 (2H, br, d, J=6Hz, $\underline{CH_2}NHCOCH_3$), 5.27 (2H, br. s, $C_{15}$—H), 5.43 (2H, br. s, $C_{12}$—H), 6.46 (1H, s, OH), 7.33 (1H, s, $C_7$—H), 7.67 (1H, d, J=8.5 Hz, $C_5$—H or $C_6$—H), 7.91 (1H, d, J=8.5 Hz, $C_6$—H or $C_5$—H), IR $\nu_{max}^{KBR}$ cm$^{-1}$: 3406, 1758, 1670, 1617, 1554, Elemental analysis for $C_{25}H_{23}N_3O_5S.3/4H_2O$:
Calculated: C 61.15; H 5.03; N 8.56
Found: C, 61.25; H, 4.97; N, 8.36.

EXAMPLE 18

Preparation of 4-aminomethyl-1,2-dihydro-9-ethyl-9-hydroxy-12H-thiino[4,3,2,-de]pyrano[3′,4′: 6,7]indolizino[1,2-b]quinoline-10,13(9H,15H)-dione.-monohydrochloride: (in formula IA, Z=—S—, $R_1$=4—$CH_2NH_2$, $R_2$=H, $R_3$=Et)

The compound prepared in Example 16 in the amount of 50 mg was suspended in 40 ml of 50% ethanol-dioxane. To the suspension 2 ml of concentrated hydrochloric acid and 50 mg of platinic oxide were added, and catalytic hydrogenation reaction was conducted. After filtration of the catalyst, the filtrate was evaporated to dryness. To the residue 10 ml of 10% hydrochloric acid was added and the insoluble materials were removed by filtration. The solvent was evaporated to dryness, and the residue was purified by means of high performance liquid chromatography (column: nucleocil-$C_{18}$; eluent: a mixed solvent of methanol, water, and 1N hydrochloric acid at a ratio of 100/100/3) to yield 9 mg of the title compound.

mp: above 300° C.

NMR (DMSO-$d_6$) δ: 0.89 (3H, t, J=7.0 Hz, $\underline{CH_3}CH_2$), 1.90 (2H, q, J=7.0 Hz, $CH_3\underline{CH_2}$), 3.3–3.8 (4H, m, $C_1$—H and $C_2$—H), 4.2–4.4 (2H, m, $\underline{CH_2}NH_2$), 5.29 (2H, br. s, $C_{15}$—H), 5.48 (2H, br. s, $C_{12}$—H), 6.4–6.6 (1H, m, —OH), 7.34 (1H, s, $C_8$—H), 7.85 (1H, d, J=9 Hz, $C_5$—H or $C_6$—H), 8.02 (1H, d, J=9 Hz, $C_6$—H or $C_5$—H), IR $\nu_{max}^{KBR}$ cm$^{-1}$: 3450, 1740, 1660, Elemental analysis for $C_{23}H_{21}N_3O_4S$ HCl.3/4H_2O:
Calculated: C 56.94; H 4.88; N 8.66;
Found: C 57.03; H 4.92; N 8.54.

EXAMPLE 19

Preparation of 4-acetylamino-1,2-dihydro-9-ethyl-9-hydroxy-12H-thiino[4,3,2,-de]pyrano[3′,4′: 6,7]indolizino-[1,2-b]quinoline-10,13(9H,15H)-dione: (in formula IA, Z=—S—, $R_1$=4-NHAc, $R_2$=H, $R_3$=Et)

(1) 8-acetylamino-5-amino-4-thiochromanone:

In 100 ml of dichloromethane 2.88 g of 5,8-diamino-4-thiochromanone was dissolved. To the solution was added 2.07 ml of triethylamine. The mixture was cooled by ice and salt, and 20 ml of dichloromethane containing 1.05 ml of acetyl chloride was added in 1 hour. After completion of the addition, the stirring was continued for another 1 hour. Chloroform was added to dissolve the precipitate, the chloroform layer was washed with water and then with saturated sodium chloride aqueous solution, and dried over anhydrous sodium sulfate. The solvent was evaporated to dryness, and the residue was subjected to silica gel column chromatography using a mixture of chloroform-ethyl acetate (ratio; 2:1) as an eluent and the solvent was evaporated from the fractions containing the title compound. Thus, 2.76 g of the title compound was obtained as the crystals having a pistachio color.

NMR (CDCl$_3$) δ: 2.17 (3H, s, CO$\underline{CH_3}$), 2.8–3.3 (4H, m, $C_2$—H and $C_4$—H), 6.40 (1H, d, J=9.0 Hz, $C_6$—H), 7.39 (1H, d, J=9.0 Hz, $C_7$—H)

(2) 4-acetylamino-1,2-dihydro-9-ethyl-9-hydroxy-12H-thiino[4,3,2,-de]pyrano[3′,4′: 6,7]indolizino[1,2-b]quinoline-10,13(9H,15H)-dione:

The solution of 40 ml of toluene and 300 mg of the compound prepared in (1) above, 300 mg of 7,8-dihydro-4-ethyl-4-hydroxy-1H-pyrano[3,4-f]indolizine-3,6,10(4H)-trione, and a small amount of p-toluenesulfonic acid was refluxed for 6 hours using a Deanstark apparatus. After cooling, the deposited crystals were collected by filtration, washed thoroughly with ethyl acetate, chloroform, ethanol, and ether successively, and dried to yield 352 mg of the title compound.

mp: above 300° C.

NMR (DMSO-$d_6$) δ: 0.89 (3H, t, J=7.2 Hz, $\underline{CH_3}CH_2$), 1.88 (2H, q, J=7.2 Hz, $CH_3\underline{CH_2}$, 2.12 (3H, s, NH$\underline{CH_3}$), 3.1–3.7 (4H, m, $C_1$—H and $C_5$—H), 5.27 (2H, br. s, $C_{15}$—H), 5.43 (2H, br. s, $C_{12}$—H), 6.49 (1H, s, OH), 7.32 (1H, s, $C_8$—H), 7.74 (1H, d, J=9 Hz, $C_5$—H or $C_6$—H), 7.89 (1H, d, J=9 Hz, $C_6$—H or $C_5$—H)

IR $\nu_{max}^{KBR}$ cm$^{-1}$: 3430, 1745, 1700, 1655, 1605

Elemental analysis for $C_{24}H_{21}N_3O_5S.1/4H_2O$:
Calculated: C 61.59; H 4.63; N 8.98
Found : C 61.88; H 4.72; N 8.93.

EXAMPLE 20

Preparation of 4-amino-1,2-dihydro-9-ethyl-9-hydroxy-12H-thiino[4,3,2,-de]pyrano[3′,4′: 6,7]indolizino[1,2-b]quinoline-10,13(9H,15H)-dione: (in formula IA, Z=—S—, $R_1$=4—$NH_2$, $R_2$=H, $R_3$=Et)

The compound prepared in Example 19 in an amount of 352 mg was dissolved in 4 ml of 60% sulfuric acid and the solution was stirred at 100° C. for 2 hours. The reaction mixture was charged into ice water, which was made alkaline with 10% sodium hydroxide aqueous solution. A yellow precipitate was collected by filtration, thoroughly washed with water, ethanol, ethyl acetate, chloroform, and ether successively, and dried to yield 257 mg of the title compound as a yellow powder.

mp: 260°–262° C. (dec.)

NMR (DMSO-$d_6$) δ: 0.88 (3H, t, J=7.2 Hz, $\underline{CH_3}CH_2$), 1.87 (2H, q, J=7.2 Hz, $CH_3\underline{CH_2}$), 3.0–3.6 (4H, m, $C_1$—H and $C_2$—H), 5.18 (2H, s, $C_{15}$—H), 5.40 (2H, s, $C_{12}$—H), 5.65 (2H, br. s, $NH_2$), 6.43 (1H, s, OH), 7.20 (1H, s, $C_8$—H), 7.31 (1H, d, J=9.2 HZ, $C_5$—H or $C_6$—H), 7.70 (1H, d, J=9.2 Hz, $C_6$—H or $C_5$—H)

IR $\nu_{max}^{KBR}$ cm$^{-1}$: 3460, 3358, 1746, 1656, 1596, 1158

Elemental analysis for $C_{22}H_{19}N_3O_4S.1/4H_2O$:
Calculated: C 62.03; H 4.61; N 9.86;
Found: C 61.75; H 4.35; N 9.56.

EXAMPLE 21

Preparation of 1,2-dihydro-9-ethyl-9-hydroxy-12H-thiino[4,3,2,-de]-pyrano[3',4':6,7]indolizino[1,2-b]-quinoline-10,13(9H,15H)-dione: (in formula IA, Z=—S—, $R_1$=H, $R_2$=H, $R_3$=Et)

(1) 5-amino-4-thiochromanone:

In 55 ml of 10% hydrochloric acid 1 g of 5-acetylamino8-amino-4-thiochromanone was suspended. To the suspension was added 10 ml of an aqueous solution containing 320 mg of sodium nitrite under cooling on an ice-salt bath, and the mixture was stirred for 30 minutes, and the whole was charged into 9 ml of cold hypophosphorous acid. The mixture was stirred at 10° C. for 10 minutes, followed by further stirring at room temperature for 2 days. The reaction mixture was extracted with chloroform, and the extract was washed with water and then with saturated sodium chloride aqueous solution, and dried over anhydrous sodium sulfate. After distilling off the solvent, the residue was subjected to silica gel column chromatography eluting with a mixture of hexane-chloroform (1:1). The solvent was evaporated from the fractions containing the title compound and its acetylated isomer. To the residue 5 ml of concentrated hydrochloric acid was added and the mixture was stirred at 80° C. for 2 hours. The mixture was made alkaline with 10% sodium hydroxide aqueous solution, washed with water and saturated sodium chloride aqueous solution, and dried over anhydrous sodium sulfate. The residue was subjected to silica gel column chromatography using a mixture of hexane-chloroform (1:1) as an eluent. The fraction containing the target compound was evaporated to yield 280 mg of the title compound as a yellow oil.

NMR (CDCl$_3$) δ: 2.9–3.0 (4H, m, C$_2$—H and C$_3$—H), 6.35 (1H, dd, J=7.8 Hz, 1.1 Hz, C$_6$—H), 6.52 (1H, dd, J=7.8 Hz, 1.1 Hz, C$_8$—H), 7.05 (1H, t, J=7.8 Hz, C$_7$—H)

(2) 1,2-dihydro-9-ethyl-9-hydroxy-12H-thiino[4,3,2,-de]-pyrano[3',4': 6,7]indolizino[1,2-b]quinoline-10,13-(9H,15H)-dione:

The solution of 30 ml of toluene and 276 mg of the compound prepared in (1) above, 400 mg of 7,8-dihydro-4-ethyl-4-hydroxy-1H-pyrano[3,4-f]indolizine-3,6,10(4H)-trione, and 170 mg of p-toluenesulfonic acid was refluxed for 4.5 hours using a Deanstark apparatus. After cooling, the deposited crystals were collected by filtration, washed thoroughly with ethyl acetate, chloroform, 50% water-methanol, methanol, and ether successively, and recrystallized from acetic acid to yield 273 mg of the title compound.

mp: 298°–300° C. (dec.)

NMR (DMSO-d$_6$) δ: 0.89 (3H, t, J=7.2 Hz, CH$_3$CH$_2$), 1.92 (2H, q, J=7.0 Hz, CH$_3$CH$_2$, 3.1–3.7 (4H, m, C$_1$—H and C$_2$—H), 5.24 (2H, s, C$_{15}$—H), 5.43 (2H, s, C$_{12}$—H), 6.50 (1H, s, OH), 7.33 (1H, s, C$_6$—H), 7.50 (1H, dd, J=1.8 Hz, 7.5 Hz, C$_6$—H), 7.68 (1H, t, J=7.5 Hz, C$_5$—H), 7.90 (1H, dd, J=1.8 Hz, 7.5 Hz, C$_4$—H)

IR $\nu_{max}^{KBR}$ cm$^{-1}$: 3538, 1746, 1662, 1614,

Elemental analysis for C$_{22}$H$_{18}$N$_2$O$_4$S.3/4CH$_3$CO$_2$H:

Calculated: C 62.52; H 4.69; N 6.20;

Found: C 62.68; H 4.56; N 6.10.

EXAMPLE 22

Preparation of 1,2-dihydro-9-ethyl-4-(4-formylpiperazine-1-yl)-9-hydroxy-3H,12H-pyrano[3',4': 6,7]indolizino[1,2-c]-benzo[ij][2,7]naphthilidine-10,13(9H,15H)-dione: (in formula IA, Z=—NH—, $R_1$=

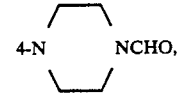

$R_2$=H, $R_3$=Et)

(1) 3-amino-4-(4-formylpiperazine-1-yl)nitrobenzene:

2-Chloro-5-nitroaniline in the amount of 57 g was dissolved in 250 ml of N,N-dimethylformamide. To the solution was added 86 g of anhydrous piperazine and stirred under heating at 150° C. for 48 hours. Water was added to the reaction mixture, which was then extracted with chloroform. The extract was washed with water and dried. The solvent was evaporated to dryness and ether was added to the residue. The deposited crystals were collected by filtration to yield 20.4 g of the title compound.

mp: 180°–190° C.

NMR (DMSO-d$_6$) δ: 2.6–3.8 (8H, m, piperazine—H), 5.43 (2H, br. s, NH$_2$), 6.99 (1H, d, J=8.7 Hz, C$_5$—Hz), 7.44 (1H, dd, J=8.7 Hz, 2.6 Hz, C$_6$—H), 7.57 (1H, d, J=2.6 Hz, C$_2$—H), 8.08 (1H, s, CHO)

IR $\nu_{max}^{KBR}$ cm$^{-1}$: 1662, 1512, 1335

Elemental analysis for C$_{11}$H$_{14}$N$_4$O$_3$S.1/4H$_2$O:

Calculated: C 51.86; H 5.75; N 21.99;

Found: C 51.89; H 5.61; N 21.59.

(2) 3-ethoxycarbonylethylamino-4-(4-formylpiperazine-1-yl)-nitrobenzene:

In 25 ml of N,N-dimethylformamide 2.5 g of the compound prepared in (1) above was dissolved. To the solution were added 1.5 g of sodium iodide, and subsequently under heating at 120° C. and while stirring, 830 mg of potassium carbonate anhydride and 1.9 ml of ethyl β-bromopropionate. One hour thereafter, the same amounts of anhydrous potassium carbonate and ethyl β-bromopropionate were again added to the mixture, and the whole was heated at 120° C. with vigorous stirring overnight. The solvent was evaporated to dryness and chloroform was added to the residue. The solvent was evaporated to dryness and the residue was subjected to silica gel column chromatography using a mixture of chloroform-methanol (50:1) as eluent to yield the fractions containing the title compound. Through evaporating the solvent from the fractions, 1.0 g of the title compound was obtained.

NMR (CDCl$_3$) δ: 1.28 (3H, t, J=7 Hz, CH$_2$CH$_3$), 2.69 (2H, t, J=6 Hz, NHCH$_2$CH$_2$), 2.8–4.0 (10H, m, NHCH$_2$CH$_2$, piperazine—H), 4.18 (2H, q, J=7 Hz CH$_2$CH$_3$), 5.24 (1H, t, NH), 6.95 (1H, d, J=9 Hz, C$_5$H), 7.43 (1H, d, J=2 Hz, C$_2$—H), 7.59 (1H, dd, J=9 Hz, 2 Hz, C$_6$—H), 8.11 (1H, s, CHO)

IR $\nu_{max}^{KBR}$ cm$^{-1}$: 1732, 1674, 1522, 1338

(3) 3-carboxylethylamino-4-(4-formylpiperazine-1-yl)-nitrobenzene:

In 10 ml of methanol 1.0 g of the compound prepared in (2) above was dissolved. To the solution were added 4.4 ml of 1N solution of sodium hydroxide aqueous solution, and then 2 hours later, 4.5 ml of 1N hydrochloric acid. After the organic solvent was evaporated to, the precipitate was collected by filtration, and washed with water and ether to yield 0.8 g of the title compound.

NMR (DMSO-d$_6$) δ: 2.5-3.1 (4H, m, NHC$\underline{H_2}$CH$_2$), 3.1-3.9 (8H, m, piperazine—H), 5.63 (1H, t, NH), 7.08 (1H, d, J=8 Hz, C$_5$—H), 7.33 (1H, d, J=2 Hz, C$_2$—H), 7.51 (1H, dd, J=8 Hz, 2 H=, C$_6$—H), 8.08 (1H, s, CHO)

IR $\nu_{max}^{KBR}$ cm$^{-1}$: 1719, 1626, 1338

Elemental analysis for C$_{14}$H$_{18}$N$_4$O$_5$:
Calculated: C 52.17; H 5.63; N 17.38;
Found: C 51.96; H 5.78; N 17.25.

(4) 3-carboxylethylamino-4-(4-formylpiperazine-1-yl)-aminobenzene:

In 30 ml of ethanol and 30 ml of dioxane 700 mg of the compound prepared in (3) above was dissolved. To the solution was added 100 mg of platinic oxide and the mixture was catalytically hydrogenated. After removal of the catalyst, the residue was evaporated and solidified with chloroform-methanol-ether. The precipitate was collected by evaporation to yield 530 mg of the title compound.

NMR (DMSO-d$_6$) δ: 2.4-3.8 (12H, m, NHC$\underline{H_2}$CH$_2$, piperazine—H), 5.82 (1H, dd, J=8 Hz, 2 Hz, C$_6$—H), 5.91 (1H, d, J=2 Hz, C$_2$—H), 6.63 (1H, d, J=8 Hz, C$_5$—H), 8.02 (1H, s, CHO)

IR $\nu_{max}^{KBR}$ cm$^{-1}$: 1716, 1644, 1521

Elemental analysis for C$_{14}$H$_{20}$N$_4$O$_3$.1/2H$_2$O:
Calculated: C 55.80; H 7.03; N 18.59;
Found: C 56.07; H 7.22; N 17.98.

(5) 5-amino-8-(4-formylpiperazine-1-yl)-2,3-dihydroquinolin-4(1H)-one:

A mixture of 12 g of polyphosphoric acid and 1.2 g of the compound prepared in (4) above was heated with stirring at 100° C. for 30 minutes. The reaction mixture was charged into water, and the mixture was neutralized with potassium carbonate and extracted with chloroform. The extract was washed with water and dried. The solvent was evaporated to dryness. The residue was subjected to silica gel column chromatography using a mixture of chloroform-methanol (30:1) as an eluent to obtain the fractions containing the title compound. The solvent was evaporated to from the fractions to yield 0.27 g of the title compound.

NMR (CDCl$_3$) δ: 2.4-3.8 (12H, m, C$_2$—H, C$_3$—H, piperazine-H), 4.3-4.6 (1H, br. s, NH), 5.60 (2H, br. s, NH$_2$), 5.85 (1H, d, J=9 Hz, arom—H), 6.92 (1H, d, J=9 Hz, arom—H), 8.08 (1H, s, CHO)

IR $\nu_{max}^{KBR}$ cm$^{-1}$: 1668, 1611, 1500

Elemental analysis for C$_{14}$H$_{18}$N$_4$O$_2$.1/3H$_2$O:
Calculated: C 59.98; H 6.71; N 19.99;
Found: C 59.94; H 6.67; N 19.59.

(6) 1,2-dihydro-9-ethyl-4-(4-formylpiperazine-1-yl)-9-hydroxy-3H,12H-pyrano[3′,4′:6,7]indolizino[1,2-c]-benzo[ij][2,7]naphthilidine-10,13(9H,15H)-dione:

In 20 ml of acetic acid were dissolved 2.0 g of the compound prepared in (5) above and 2.3 g of 7,8-dihydro-4-ethyl-4-hydroxy-1H-pyrano[3,4-f]indolizine-3,6,10(4H)-trione. The solution was heated with stirring under nitrogen stream at 100° C. for 6 hours. The reaction mixture was condensed and the residue was subjected to silica gel chromatography using a mixture of chloroform-methanol (50:1) as an eluent to obtain the fractions containing the title compound. The solvent was evaporated from the fractions, 335 mg of the title compound was obtained.

mp: 210°-215 ° C. (dec.)

NMR (CDCl$_3$) δ: 1.01 (3H, t, J=7 Hz, CH$_2$C$\underline{H_3}$), 1.6-2.3 (2H, m, C$\underline{H_2}$CH$_3$), 2.4-4.2 (12H, m, piperazine—H, C$_1$—H, C$_2$—H), 5.17 (2H, s, C$_{15}$—H), 5.29, 5.70 (2H, ABq, J=17 Hz, c$_{12}$—H), 7.53 (1H, s, arom—H), 7.54 (1H, s, arom-H), 7.64 (1H, s, arom—H), 8.14 (1H, s, CHO)

IR $\nu_{max}^{KBR}$ cm$^{-1}$: 1749, 1662, 1605

Elemental analysis for C$_{27}$H$_{27}$N$_5$O$_5$.9/4H$_2$O:
Calculated: C 59.83; H 5.86; N 12.92;
Found: C 59.77; H 5.69; N 12.46.

EXAMPLE 23

Preparation of 1,2-dihydro-9-ethyl-9-hydroxy-4-(piperazine-1-yl)-3H,12H-pyrano[3′,4′:6,7]indolizino[1,2-c]-benzo[ij][2,7-]naphthilidine-10,13(9H,15H)-dione.dihydrochloride:

(in formula IA,

Z=—NH—, R$_1$=

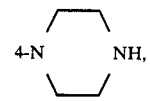

R$_2$=H, and R$_3$=Et)

The solution of 300 mg of the compound prepared in Example 22 in 3 ml of 6N hydrochloric acid was stirred at 100° C. for 30 minutes. The reaction mixture was condensed and the residue obtained was subjected to high performance column chromatography [column: nucleocil-C$_{18}$; eluent: a mixed solvent of methanol and water (3:7) adjusted to pH 3 with hydrochloric acid] to yield 225 mg of the title compound.

mp: 220°-240° C. (dec.)

NMR (DMSO-d$_6$) δ: 0.88 (3H, t, J=7.0 Hz, CH$_2$C$\underline{H_3}$), 1.6-2.1 (2H, m, C$_2$CH$_3$), 2.8-5.2 (12H, m, piperazine—H, C$_1$—H , C$_2$—H), 5.24 (2H, s, C$_{15}$—H or C$_{12}$—H), 5.43 (2H, s, C$_{15}$—H or C$_{12}$—H), 7.48 (1H, s, C$_8$—H), 7.44 (1H, d, J=9 Hz, arom—H), 7.64 (1H, d, J=9 Hz, arom—H)

IR $\nu_{max}^{KBR}$ cm$^{-1}$: 1760, 1675, 1630

Elemental analysis for C$_{26}$H$_{27}$N$_5$O$_4$.2HCl.11/4H$_2$O:
Calculated: C 52.40; H 5.83; N 11.75;
Found: C 52.47; H 5.40; N 11.50.

EXAMPLE 24

Preparation of 1,2-dihydro-9-ethyl-9-hydroxy-4-methoxy-12H-thiino[4,3,2,-de]pyrano[3′,4′:6,7]indolizino[1,2-b]-quinoline-10,13(9H,15H)-dione: (in formula IA, Z=—S—, R$_1$=4—OMe, R$_2$=H, R$_3$=Et)

(1) 5-acetylamino-8-hydroxy-4-thiochromanone:

In 13 ml of 35% sulfuric acid 3 g of 5-acetylamino-8-amino-4-thiochromanone was dissolved. To the solution was added 10 ml of ice water, and, while stirring at 0° C., 13 ml of an aqueous solution of 1.12 g of sodium nitrite was further added dropwise. Stirring was continued for further 30 minutes, a small amount of urea was added to the reaction mixture, and then the whole was charged into 500 ml of 32% copper nitrate aqueous solution with vigorous stirring. Subsequently, 1.69 g of cuprous oxide was added, and the mixture was stirred for 30 minutes, extracted with chloroform. The mixture was dried over anhydrous sodium sulfate. The solvent was evaporated and the residue was subjected to silica gel column chromatography using a mixture of hexane-ethyl acetate (1:1) as an eluent. The solvent was removed from the fraction containing the target compound to yield 290 mg of the title compound.

NMR (CDCl$_3$) δ: 2.23 (3H, s, CO$\underline{CH_3}$), 3.0-3.4 (4H, m, C$_2$—H and C$_3$—H), 7.09 (1H, d, J=9.2 Hz, C$_7$—H), 8.40 (1H, d, J=9.2 Hz, C$_6$—H)

(2) 5-acetylamino-8-methoxy-4-thiochromanone:

In 20 ml of acetone 180 mg of the compound prepared in (1) above, 0.1 ml of methyl iodide, and 110 mg of potassium carbonate were added, and the mixture was refluxed for 3.5 hours. After removing the solvent, ethyl acetate was added to the residue, and the mixture was washed with water and saturated sodium chloride aqueous solution, and dried over anhydrous sodium sulfate. Upon removal of the solvent by distillation, the residue was subjected to silica gel column chromatography using a mixture of chloroform-ethyl acetate (5:1) as an eluent. The solvent was removed from the fraction containing the target compound and 174 mg of the title compound was obtained.

NMR (CDCl$_3$) δ: 2.21 (3H, s, CO$\underline{CH_3}$), 2.9-3.4 (4H, m, C$_2$—H and C$_3$—H), 3.90 (3H, s, OCH$_3$), 7.00 (1H, d, J=9.3 Hz, C$_7$—H), 8.45 (1H, d, J=9.3 Hz, C$_6$—H)

(3) 5-amino-8-methoxy-4-thiochromanone:

The compound prepared in (2) above weighing 172 mg was dissolved in 3 ml of 35% sulfuric acid, and the solution was stirred at 50°-60° C. for 5 hours. After cooling, the mixture was and neutralized with sodium bicarbonate. The mixture was extracted three times with chloroform, and extract washed with water and saturated sodium chloride aqueous solution, and dried over anhydrous sodium sulfate. After distilling off the solvent, the residue was subjected to silica gel column chromatography using a mixture of hexane-ethyl acetate (5:1). Through condensation of the fraction containing the title compound 123 mg of the title compound was obtained.

NMR (CDCl$_3$) δ: 2.8-3.3 (4H, m, C$_2$—H and C$_3$—H), 3.80 (3H, s, OCH$_3$), 6.35 (1H, d, J=9.0 Hz, C$_6$—H or C$_7$—H), 6.89 (1H, d, J=9.0 Hz, C$_7$—H or C$_6$—H)

(4) 1,2-dihydro-9-ethyl-9-hydroxy-4-methoxy-12H-thiino[4,3,2,-de]pyrano[3',4': 6,7]indolizino[1,2-b]quinoline-10,13(9H,15H)-dione:

In 5 ml of acetic acid were dissolved 120 mg g of the compound prepared in (3) above and 150 mg of 4-ethyl-7,8-dihydro-1H-pyrano[3,4-f]indolizine-3,6,10(4H)-trione. The solution was refluxed under heating for 4 hours, and then cooled. The precipitate was collected by filtration, washed thoroughly with ethyl acetate and chloroform, and dried to yield 170 mg of the title compound as yellow crystals.

Melting Point: 289°-292° C.

NMR (DMSO-d$_6$) δ: 0.88 (3H, t, J=7 Hz, $\underline{CH_2}$CH$_3$), 1.88 (2H, q, J=7 Hz, CH$_3$$\underline{CH_2}$), 3.15-3.45 (4H, m, C$_1$—H and CH$_2$), 4.02 (3H, s, OCH$_3$), 5.25 (2H, br. s, C$_{15}$—H), 5.43 (2H, br. s, C$_{12}$—H), 6.49 (1H, s, OH), 7.30 (1H, s, C$_8$—H), 7.84 (1H, d, J=9.9 Hz, C$_5$—H or C$_6$—H), 8.08 (1H, d, J=9.9 Hz, C$_6$—H or C$_5$—H)

IR $\nu_{max}^{KBR}$ cm$^{-1}$: 3466, 3100, 2938, 1743, 1659, 1602
Elemental analysis for C$_{23}$H$_{20}$N$_2$O$_5$.1/2H$_2$O:
Calculated: C 62.01; H 4.75; N 6.29;
Found: C 62.20; H 4.78, N 6.13.

EXAMPLE 25

Preparation of 1,2-dihydro-4,9-dihydroxy-9-ethyl-12H-thiino[4,3,2,-de]pyrano[3',4': 6,7]indolizino[1,2-b]-quinoline-10,13(9H,15H)-dione: (in formula IA, Z=—S—, R$_1$=4—OH, R$_2$=H, R$_3$=Et)

To 5 ml of 47% hydrobromic acid 102 mg of the compound prepared in Example 24 was added and the mixture was refluxed in nitrogen stream for 7.5 hours. The reaction mixture was charged into ice water and made alkaline with 10% sodium hydroxide aqueous solution. The insoluble materials was removed and the mixture was re-acidified with concentrated hydrochloric acid. The precipitate was collected by filtration, and washed with water, ethanol and then with ethyl acetate, and dried to yield 95 mg of the title compound as a yellow powder.

mp: above 250° C. (dec.)

NMR (DMSO-d$_6$) δ: 0.89 (3H, t, J=7 Hz, $\underline{CH_3}$CH$_2$), 1.87 (2H, q, J=7 Hz, CH$_3$$\underline{CH_2}$), 3.0-3.6 (4H, m, C$_1$—H and C$_2$—H), 5.21 (2H, br. s, C$_{15}$—H), 5.41 (2H, br. s, C$_{12}$—H), 6.43 (1H, s, C$_9$—OH), 7.26 (1H, s, C$_8$—H), 7.44 (1H, d, J=9 Hz, C$_5$—H or C$_6$—H)

IR $\nu_{max}^{KBR}$ cm$^{-1}$: 3406, 1746, 1653, 1581
Elemental analysis for C$_{22}$H$_{18}$N$_2$O$_5$S.5/4H$_2$O:
Calculated: C 59.38; H 4.64; N 6.29;
Found: C 59.36; H 4.64; N 5.99.

EXAMPLE 26

Preparation of 4-chloro-1,2-dihydro-9-ethyl-9-hydroxy-3H,12H-pyrano[3',4': 6,7]indolizino[1,2-c]benzo[i,j][2,7]-naphthilidine-10,13(9H,15H)-dione: (in formula IA, Z=—NH—, R$_1$=4—Cl, R$_3$=H, R$_3$=Et)

(1) 2-cyanomethylamino-4-nitrochlorobenzene:

In 700 ml of dichloromethane 103 g of 2-chloro-5-nitroaniline was suspended. To this suspension 55 ml of acrylonitril was added and then 8 ml of Triton B was added dropwise while stirring at room temperature. One hour later, 30 ml of acrylonitril and 5 ml of Triton B were further added, and the mixture was stirred overnight. Chloroform was added to the reaction mixture, which was washed with water, and dried. The mixture was condensed and ether was added to the condensate. The precipitate was collected by filtration to yield 65 g of the title compound.

mp: 130°-140° C.

NMR (CDCl$_3$) δ: 2.74 (2H, t, J=6.5 Hz, CH$_2$CN), 3.67 (2H, q, J=6.5 Hz, NH$\underline{CH_2}$), 4.5-5.3 (1H, br, NH), 7.2-7.8 (3H, m, arom—H)

IR $\nu_{max}^{KBR}$ cm$^{-1}$: 2254, 1533, 1344
Elemental analysis for C$_9$H$_8$N$_3$O$_2$Cl:
Calculated: C 47.91; H 3.57; N 18.62;
Found: C 47.87; H 3.53; N 18.69.

(2) 2-carboxymethylamino-4-nitrochlorobenzene:

A mixture of 65 g of the compound prepared in (1) above, 130 ml of acetic acid and 325 ml of concentrated hydrochloric acid was heated with stirring for 30 minutes at 80° C., and then cooled. Water was added to the reaction mixture. The precipitate was collected by filtration and washed with water and ether to yield 55 g of the title compound.

mp: 160°-162° C.

NMR (CDCl$_3$+CD$_3$OD) δ: 2.69 (2H, t, J=6 Hz, CH$_2$CN), 3.57 (2H, t, J=6 Hz, NH$\underline{CH_2}$), 7.2-7.8 (3H, m, arom—H)

IR $\nu_{max}^{KBR}$ cm$^{-1}$: 1719, 1530, 735

Elemental analysis for $C_9H_9N_2O_4Cl.1/5H_2O$:
Calculated: C 43.54; H 3.82; N 11.28; Cl 14.28;
Found: C 43.79; H 3.50; N 11.53; Cl 14.87.

(3) 4-amino-2-carboxyethylaminochlorobenzene:

The compound prepared in (2) above in the amount of 10 g was dissolved in 260 ml of a mixture of ethanol-dioxane (1:1), and was catalytically hydrogenated using Raney nickel as a catalyst. After removing the catalyst, the filtrate was condensed to yield 10 g of the title compound.

mp: 90°–105° C.

NMR ($CDCl_3+CD_3OD$) δ: 2.63 (2H, t, J=6.5 Hz, $CH_2CN$), 3.43 (2H, t, J=6.5 Hz, $NHCH_2$), 6.07 (1H, s, arom—H), 6.0–6.4 (1H, s, arom—H), 7.0–7.3 (1H, arom—H), IR $\nu_{max}^{KBR}$ cm$^{-1}$: 1608, 1512, 633

Elemental analysis for $C_9H_{11}N_2O_2Cl.1/4H_2O$:
Calculated: C 49.32; H 5.06; N 12.78;
Found: C 49.48; H 5.36; N 12.76.

(4) 1H-5-amino-4-oxo-8-chloro-2,3-dihydroquinoline:

A mixture of 100 g of polyphosphoric acid and 9.0 g of the compound prepared in (3) above was heated with stirring for 1 hour. The reaction mixture was charged in water, and the whole was neutralized with potassium carbonate, extracted with chloroform. The extract was dried and the solvent was evaporated. The residue was purified by means of silica gel column chromatography to yield 2.55 g of the title compound.

NMR ($CDCl_3$) δ: 2.68 (2H, t, J=7.5 Hz, $CH_2CN$), 3.58 (2H, t, J=7.5 Hz, $NHCH_2$), 5.86 (1H, d, J=8.5 Hz, arom—H), 4.0–7.0 (3H, br, NH, $NH_2$), 7.06 (1H, d, J=8.5 Hz, arom—H)

(5) 4-chloro-1,2-dihydro-9-ethyl-9-hydroxy-3H,12H-pyrano-[3',4': 6,7]indolizino[1,2-c]benzo[i,j][2,7]naphthilidine- 10,13(9H,15H)-dione:

In 5 ml of acetic acid were dissolved 350 mg of the compound prepared in (4) above and 468 mg of 7,8-dihydro-4-ethyl-4-hydroxy-1H-pyrano[3,4-f]indolizine-3,6,10(4H)-trione, and the solution was stirred at 90° C. for 5 hours. After cooling, the precipitate was collected by filtration and dissolved in chloroform-methanol. Then, ether was added to the solution and the precipitate was collected by filtration to yield 60 mg of the title compound.

Melting Point: 230°–240° C. (dec.)

NMR ($CDCl_3+CD_3OD$) δ: 1.04 (3H, t, J=7 Hz, $CH_2CH_3$), 1.7–2.2 (2H, m, $CH_2CH_3$), 3.6–3.9 (2H, m, $CH_2$), 5 22 (2H, s, $C_{15}$—H), 5.32, 5.67 (2H, ABq, J=16 Hz, $C_{12}$—H), 7.4–7.8 (2H, $C_5$—H, $C_6$—H), 7.72 (1H, s, $C_8$—H)

IR $\nu_{max}^{KBR}$ cm$^{-1}$: 1746, 1662, 1608

Elemental analysis for $C_{22}H_{18}N_3O_4Cl.1/2H_2O$:
Calculated: C 61.05; H 4.42; N 9.71; Cl 8.21;
Found: C 60.92; H 4.40; N 9.69; Cl 8.87.

EXAMPLE 27

Preparation of 3-acetyl-1,2-dihydro-9-ethyl-9-hydroxy-12H-pyrano[3',4': 6,7]indolizino[1,2-c]benzo[i,j][2,7]-naphthilidine- 10,13(9H,15H)-dione: (in formula IA, Z=—NAc—, $R_1$=4—OMe, $R_2$=H, $R_3$=Et)

(1) ethyl 3-(2-methoxy-5-nitroanilino) propionate:

On hundred (100) gram of 2-ethoxy-5-nitroaniline was kept melting by heating to 120°–130° C., to this was added 50 g of sodium bicarbonate, and then 100 ml of ethyl β-bromopropionate dropwise in 2 hours. The mixture was further stirred at the same temperature for 2 hours. After cooling, ethyl acetate was added to the reaction mixture, which was then washed with water and saturated sodium chloride aqueous solution, and dried over anhydrous sodium sulfate. The solvent was removed. Ether was added to the residue and the deposited crystals were collected by filtration. The title compound in an amount of 75.66 g was obtained by recrystallizing from a mixed solvent of ethanol-hexane.

NMR ($CDCl_3$) δ: 1.27 (3H, t, J=7.0 Hz, $CH_3CH_2$), 2.66 (2H, t, J=6.2 Hz, $C_2$—H), 3.60 (2H, t, J=6.2 Hz, $C_3$—H), 3.94 (3H, s, $OCH_3$), 4.18 (2H, q, J=7.0 Hz, $CH_3CH_2$), 6.75 (1H, d, J=8.8 Hz, $C_3'$—H), 7.41 (1H, d, J=2.6 Hz, $C_6'$—H), 7.63 (1H, dd, J=8.8 Hz, 2.6 Hz, $C_4'$—H)

(2) 3-(2-methoxy-5-nitroanilino) propionic acid:

To a mixture of 100 ml of ethanol and 10 g of the compound prepared in (1) above was added 40 ml of 1N sodium hydroxide aqueous solution, and the mixture was stirred for 1 hour. After condensing the mixture to a volume of approximately 30 ml, 70 ml of water was added. The mixture was neutralized with hydrochloric acid. The precipitate was collected by filtration, and recrystallized from 10% ethanol-water to yield 8.6 g of the title compound.

NMR ($CDCl_3$) δ: 2.74 (2H, t, J=6.3 Hz, $C_2$—H), 3.56 (2H, t, J=6.3 Hz, $C_3$—H), 3.94 (3H, s, $OCH_3$), 6.76 (1H, d, J=8.7 Hz, $C_3'$—H), 7.42 (1H, d, J=2.6 Hz, $C_6'$—H), 7.66 (1H, dd, J=8.7 Hz, 2.6 Hz, $C_4'$—H)

(3) 5-amino-8-methoxy-2,3-dihydroquinolin-4(1H)-one:

The compound of the amount of 8.59 g prepared in (2) above was dissolved in a mixed solvent consisting of 130 ml dioxane, 130 ml of ethanol, and 5 ml of concentrated hydrochloric acid. Five hundred (500) mg of platinic oxide was added to the solution to effect catalytic hydrogenation. The catalyst A was removed by filtration. The solvent was evaporated to dryness to yield a crude powder of 3-(5-amino-2-methoxyanilino)-propionic acid hydrochloride, which was added to 250 g of polyphosphoric acid heated to a temperature of 110°–120° C. in 20 minutes. This mixture was stirred at the temperature for 3 hours, and allowed to cooled. The reaction mixture was charged into ice water, neutralized with sodium bicarbonate, and extracted three times with ethyl acetate. The extract was washed with water and saturated sodium chloride aqueous solution, and then dried over anhydrous sodium sulfate. After removing the solvent, the residue was subjected to silica gel column chromatography using a mixture of hexane-ethyl acetate (3:1). Upon condensation of the fractions containing the title compound, 2.14 g of the title compound was obtained.

NMR ($CDCl_3$) δ: 2.73 (2H, t, J=7 Hz, $C_3$—H), 3.79 (2H, t, J=7 Hz, $C_2$—H), 3.81 (3H, s, $OCH_3$), 5.92 (1H, d, J=9 Hz, $C_6$—H or $C_7$—H), 6.88 (1H, d, J=9 Hz, $C_7$—H or $C_6$—H)

(4) 5-benzyloxycarbonylamino-8-methoxy-2,3-dihydroquinolin-4(1H)-one:

In 20 ml of methylene chloride 1.28 g of the compound prepared in (3) above was dissolved. To this solution 0.6 ml of pyridine and 1.1 ml of benzyloxycarbonylchloride were added and the solution was stirred at room temperature for 1 hour. The reaction mixture was washed with water and saturated sodium chloride aqueous solution, and dried over anhydrous sodium sulfate. After evaporating the solvent, the residue was subjected to silica gel column chromatography using a mixture of hexane-ethyl acetate (4:1) as an eluent. The fractions containing the title compound was condensed and hexane was added to the condensate. The crystals were collected by filtration to yield 1.87 g of the title compound by filtration.

NMR (CDCl$_3$) δ: 2.70 (2H, t, J=7 Hz, C$_3$—H), 3.56 (2H, t, J=7 Hz, C$_2$—H), 3.83 (3H, s, OCH$_3$), 5.19 (2H, s, CH$_2$Ar), 6.84 (1H, d, J=9 Hz, C$_7$—H), 7.2-7.55 (5H, m, Ar), 7.60 (1H, d, J=9 Hz, C$_6$—H)

(5) 1-acetyl-5-benzyloxycarbonylamino-8-methoxy-2,3-dihydroquinolin-4(1H)-one:

In 20 ml of methylene chloride 510 mg of the compound prepared in (4) above was dissolved. To this solution 1.2 ml of triethylamine and 1.0 ml of acetyl chloride were added and the solution was refluxed for 1 hour. The reaction mixture was washed with water and saturated sodium chloride aqueous solution, and dried over anhydrous sodium sulfate. The solvent was removed to yield 566 mg of the title compound was obtained.

NMR (CDCl$_3$) δ: 2.05 (3H, s, COCH$_3$), 2.6-3.6 (4H, m, C$_2$—H, and C$_3$—H), 3.86 (3H, s, OCH$_3$), 5.21 (2H, s, —CH$_2$Ar), 7.2-7.6 (6H, m, C$_7$—H and Ar), 8.33 (1H, d, J=9 Hz, C$_6$—H)

(6) 1-acetyl-5-amino-8-methoxy-2,3-dihydroquinolin-4(1H)-one:

In 40 ml of a mixture of ethanol-dioxane (1:1) 560 mg of the compound prepared in (5) above was dissolved. To this 100 mg of 10% palladium-carbon was added to perform catalytic hydrogenation. The catalyst was removed by filtration and the solvent was evaporated. The residue was subjected to silica gel column chromatography using a mixture of hexane-ethyl acetate (1:1) as an eluent. The fractions containing the title compound was evaporated to yield 358 mg of the title compound.

NMR (CDCl$_3$) δ: 2.07 (3H, s, COCH$_3$), 2.3-3.0 (2H, m, C$_3$—H), 3.0-3.6 (1H, m, C$_2$—H), 3.77 (3H, s, OCH$_3$), 4.8-5.2 (1H, m, C$_2$—H), 6.56 (1H, d, J=9 Hz, C$_6$—H), 7.07 (1H, d, J=9 Hz, C$_7$—H)

(7) 3-acetyl-1,2-dihydro-9-ethyl-9-hydroxy-4-methoxy-12H-pyrano[3',4': 6,7]indolizino[1,2-c]benzo[i,j][2,7]-naphthilidine-10,13(3H, 9H, 15H)-dione:

In 20 ml of acetic acid were dissolved 773 mg of the compound prepared in (6) above and 780 mg of 7,8-dihydro-4-ethyl-4-hydroxy-1H-pyrano[3,4-f]indolizine-3,6,10(4H)-trione, and the solution was refluxed for 4.5 hours in a nitrogen stream. After cooling, the solvent was removed and acetone was added to the residue. The precipitate was collected by filtration and washed thoroughly with acetone, ethyl acetate, and chloroform, and dried to yield 584 mg of the title compound.

Melting Point: 292°-295° C. (dec.)

NMR (DMSO-d$_6$) δ: 0.88 (3H, t, J=7 Hz, CH$_3$CH$_2$), 1.88 (2H, q, J=7 H, H$_3$CH$_2$), 2.00 (3H, s, COCH$_3$), 3.14-3.44 (4H, m, C$_1$—H and C$_2$—H), 4.02 (3H, s, OCH$_3$), 5.25 (2H, br. s, C$_{15}$—H), 5.43 (2H, br. s, C$_{12}$—H), 6.49 (1H, s, OH), 7.30 (1H, s, C$_8$—H), 7.84 (1H, d, J=9 Hz, C$_5$—H or C$_6$—H), 8.08 (1H, d, J=9 Hz, C$_6$—H or C$_5$—H)

IR $\nu_{max}^{KBR}$ cm$^{-1}$: 3400, 2944, 1758, 1659, 1605

Elemental analysis for C$_{25}$H$_{23}$N$_3$O$_6$·3/2H$_2$O:
Calculated: C 61.47; H 5.36; N 8.60;
Found: C 61.32; H 5.26; N 8.32.

EXAMPLE 28

Preparation of 1,2-dihydro-9-ethyl-9-hydroxy-4-methoxy-12H-pyrano[3',4': 6,7]indolizino[1,2-c]benzo[i,j][2,7]-naphthilidine-10,13(3H,9H,15H)-dione: (in formula IA, Z=—NH—, R$_1$=4—OMe, R$_2$=H, R$_3$=Et)

A mixture of 5 ml of 47% hydrobromic acid and 114 mg of the compound prepared in Example 27 was refluxed in a nitrogen stream for 2 hours. The reaction mixture was charged into ice water and the precipitate was collected by centrifugation, and washed with water, acetone and then with ethanol, and dried to yield 84 mg of the title compound.

mp: above 300° C.

NMR (DMSO-d$_6$) δ: 0.88 (3H, t, J=7 Hz, CH$_3$CH$_2$), 1.86 (2H, q, J=7 Hz, CH$_3$CH$_2$), 3.1-3.8 (4H, m, C$_1$—H and C$_2$—H), 3 94 (3H, s, OCH$_3$), 5.20 (2H, br. s, C$_{15}$—H), 5.41 (2H, br. s, C$_{12}$—H), 7.27 (1H, s, C$_8$—H), 7.38 (1H, d, J=9 Hz, C$_5$—H or C$_6$—H), 7.59 (1H, d, J=9 Hz, C$_6$—H or C$_5$—H), IR $\nu_{max}^{KBR}$ cm$^{-1}$: 3412, 1746, 1659, 1608

Elemental analysis for C$_{23}$H$_{21}$N$_3$O$_5$·2H$_2$O:
Calculated: C 60.65; H 5.53; N 9.22;
Found: C 60.64; H 5.29; N 8.95.

EXAMPLE 29

Preparation of 4-acetylamino-9-ethyl-1,2-dihydro-9-hydroxy-12H-pyrano[4,3,2-de]pyrano[3',4': 6,7]indolizino-[1,2-b]quinoline-10,13(9H,15H)-dione: (in formula IA, Z=—O—, R$_1$=4—NHAc, R$_2$=H, R$_3$=Et)

(1) 2-hydroxy-4-nitrophenylacetamide:

To a solution of 1.54 g of 2-hydroxy-4-nitroaniline in 10 ml of pyridine was added 2.05 g of acetic acid anhydride, and the mixture was allowed to stand overnight. The reaction mixture was charged into ice water, and a yellow precipitate was collected by filtration, washed with water, and dried to obtain 2.12 g of yellow powder. This powder was suspended into 20 ml of methanol, and to this was added dropwise 8.9 ml of 1N sodium hydroxide aqueous solution. The mixture was stirred for 30 minutes, and neutralized with 10% hydrochloric acid. The precipitate was collected by filtration, washed with water, and dried to yield 1.4 g of the title compound as a yellow powder.

NMR (DMSO-d$_6$) δ: 2.20 (3H, s, CH$_3$), 7.75 (1H, d, J=3 Hz, C$_3$—H), 7.80 (1H, dd, J=3 and 9 Hz, C$_5$—H), 8.38 (1H, d, J=9 Hz, C$_6$—H), (2) 3-(2-acetylamino-5-nitro)phenoxy-1-propanol:

In a solution of 10 g of the compound prepared in (1) above in 200 ml of N,N-dimethylformamide was gradually added 2.5 g of 50% sodium hydride, and the solution was stirred for 20 minutes. To this was added 100 mg of 18-crown-6-ether, and then 7.2 g of 3-chloro-1-propanol dropwise. The mixture was stirred at 80° C. for 2 days. The reaction mixture was charged into ice water, extracted with ethyl acetate. The extract was washed with 10% sodium hydroxide aqueous solution and water, and then dried over anhydrous sodium sulfate. A yellow solid material was obtained by evaporating the solvent. The residue was recrystallized from a mixture of chloroform-n-hexane to yield 6.3 g of the title compound as yellow crystals.

mp: 133°-135° C.

NMR (CDCl$_3$) δ: 1.70 (1H, t, J=5 Hz, OH), 2.00–2.30 (2H, m, C$_2$—H), 2.24 (3H, s, CH$_3$), 3.94 (2H, dt, J=5 and 6 Hz, C$_1$—H), 4.32 (2H, t, J=6.5 Hz, C$_3$—H), 7.77 (1H, d, J=3 Hz, Ar), 7.90 (1H, dd, J=3 and 9 Hz), 8.28 (1H, br. s, NH), 8.58 (1H, d, J=9 Hz, Ar)

(3) 3-(2-acetylamino-5-nitro)phenoxypropionic acid:

A solution of 3.6 g of the compound prepared in (2) above in 150 ml of acetone was cooled to 0° C. About 7 ml of Jones reagent prepared from 2.67 g of chromic anhydride was gradually added, and the solution was stirred for 15 minutes. To this was then added 600 ml of water. The precipitate was collected by filtration, washed with water, and dried to yield 2.8 g of the title compound as a colorless powder.

mp: 198°–200° C.

NMR (DMSO-d$_6$) δ: 2.21 (3H, s, CH$_3$), 2.86 (2H, t, J=6.5 Hz, C$_3$—H), 4.36 (2H, t, J=6.5 Hz, C$_2$—H), 7.80–8.00 (2H, m, Ar), 8.42 (1H, d, J=9 Hz, Ar), 9.35 (1H, br. s, NH)

(4) 8-acetylamino-5-amino-4-chromanone:

The compound prepared in (3) above in the amount of 7.9 g was added to a mixture of ethanol-water (170 ml–40 ml). To this 300 mg of platinic oxide was added to perform catalytic hydrogenation. The insoluble material was removed by filtration and the solvent was evaporated to dryness to yield 7.0 g of white powder. This powder was dissolved in 30 ml of concentrated sulfuric acid, and the mixture was heated at a temperature of 80° C. for 3 hours. The mixture was charged into ice water and basified with sodium carbonate, and extracted with ethyl acetate. The extract was dried over anhydrous sodium sulfate and the solvent was evaporated. The residue was subjected to silica gel column chromatography using a mixture of chloroform-methanol (99:1) as an eluent. The fractions containing the title compound was evaporated to yield 1.5 g of the title compound as a yellow powder.

NMR (CDCl$_3$) δ: 2.17 (3H, s, CH$_3$), 2.81 (2H, t, J=7 Hz, C$_3$—H), 4.52 (2H, t, J=7 Hz, C$_2$—H), 6.25 (1H, d, J=9 Hz, C$_6$—H), 8.15 (1H, d, J=9 Hz, C$_7$—H)

(5) 4-acetylamino-9-ethyl-1,2-dihydro-9-hydroxy-12H-pyrano-[4,3,2-de]pyrano[3',4': 6,7]indolizino[1,2-b]quinoline-10,13(9H,15H)-dione:

In 3 ml of acetic acid were dissolved 70 mg of the compound prepared in (4) above and 90 mg of 4-ethyl-7,8-dihydro-4-hydroxy-1H-pyrano[3,4-f]indolizine-3,6,10(4H)-trione, and the solution was refluxed in an nitrogen stream for 5 hours. After cooling, the precipitate was collected by filtration, washed with acetone, recrystallized from acetic acid to yield 60 mg of the title compound.

Melting Point: 280°–285° C. (dec.)

IR $\nu_{max}^{KBR}$ cm$^{-1}$: 3500, 3405, 1740, 1680, 1655

Mass m/e 447 (M+), 403

EXAMPLE 30

Preparation of 4-amino-9-ethyl-1,2-dihydro-9-hydroxy-12H-pyrano[4,3,2-de]pyrano[3',4': 6,7]indolizino[1,2-b]-quinoline-10,13(9H,15H)-dione: (in formula IA, Z=—O—, R$_1$=4—NH$_2$, R$_2$=H, R$_3$=Et)

To 10 ml of 6N hydrochloric acid 50 mg of the compound prepared in Example 29 was added, and the mixture was refluxed in a nitrogen stream for 1 hour. Ethanol was added to the residue obtained by evaporating the reaction mixture to dryness. This procedure was repeated two times to yield a yellow powder, which was recrystallized from methanol to yield 40 mg of the title compound as a yellow crystalline powder.

mp: 240°–245° C. (dec.)

NMR (DMSO-d$_6$) δ: 0.98 (3H, t, J=7 Hz, CH$_3$), 5.20 (2H, s, C$_{12}$—H or C$_{15}$—H), 5.42 (2H, s, C$_{12}$—H or C$_{15}$—H), 6.43 (1H, br. s, OH), 7.23 (1H, s, C$_8$—H), 7.37 (1H, d, J=9 Hz, C$_5$—H), 7.60 (1H, d, J=9 Hz, C$_6$—H),

IR $\nu_{max}^{KBR}$ cm$^{-1}$: 3420, 3360, 1750, 1655, 1600

Elemental analysis for C$_{22}$H$_{19}$N$_3$O$_6$.1/4H$_2$O:

Calculated: C 64.46; H 4.80; N 10.25;

Found: C 64.77; H 5.11; N 10.21.

The compounds of this invention, including those prepared in the above examples and those prepared according to the same or similar manner as in the above examples, are listed in the following table.

| No. | % | m | n | R$_1$ | R$_2$ | R$_3$ |
|---|---|---|---|---|---|---|
| 1 | CH$_2$ | 1 | 0 | H | H | Et |
| 2 | CH$_2$ | 1 | 0 | 3-Me | H | Et |
| 3 | CH$_2$ | 1 | 0 | 3-HO | H | Et |
| 4 | CH$_2$ | 1 | 0 | 3-MeO | H | Et |
| 5 | CH$_2$ | 1 | 0 | 3-NO$_2$ | H | Et |
| 6 | CH$_2$ | 1 | 0 | 3-NH$_2$ | H | Et |
| 7 | CH$_2$ | 1 | 0 | 3-NH$_2$NH | H | Et |
| 8 | CH$_2$ | 1 | 0 | 3-(piperazine-1-yl) | H | Et |
| 9 | CH$_2$ | 1 | 0 | 3-(piperidine-4-yl)amino | H | Et |
| 10 | CH$_2$ | 1 | 0 | H | 4-Me | Et |
| 11 | CH$_2$ | 1 | 0 | H | 4-NH$_2$CH$_2$ | Et |
| 12 | CH$_2$ | 1 | 0 | H | 4-HOCH$_2$ | Et |
| 13 | CH$_2$ | 1 | 0 | H | 4-HO | Et |
| 14 | CH$_2$ | 1 | 0 | H | 4-NH$_2$NH | Et |
| 15 | CH$_2$ | 1 | 0 | 3-HO | 4-Me | Et |
| 16 | CH$_2$ | 1 | 0 | 3-Me | 4-NH$_2$ | Et |
| 17 | CH$_2$ | 1 | 0 | 3-Me | 3Me | Et |
| 18 | NH | 0 | 1 | 3-HO | H | Et |
| 19 | NH | 0 | 1 | 3-Me | H | Et |
| 20 | NH | 0 | 1 | 3-HO | 4-CH$_3$ | Et |
| 21 | NH | 0 | 1 | 3-NO$_2$ | H | Et |
| 22 | NH | 0 | 1 | 3-NH$_2$ | H | Et |
| 23 | NH | 0 | 1 | 3-NH$_2$NH | 4-CH$_3$ | Et |
| 24 | NH | 0 | 1 | H | 4-NH$_2$ | Et |
| 25 | NH | 0 | 1 | H | 4-NH$_2$CH$_2$ | Et |
| 26 | NH | 0 | 1 | H | 4-HOCH$_2$ | Et |

-continued

| No. | % | m | n | R₁ | R₂ | R₃ |
|---|---|---|---|---|---|---|
| 27 | NH | 0 | 1 | H | 4-HO | Et |
| 28 | NH | 0 | 1 | H | 4-NH₂NH | Et |
| 29 | NAc | 0 | 1 | H | 4-HOCH₂ | Et |
| 30 | NH | 0 | 2 | H | 4-HOCH₂ | Et |
| 31 | NH | 0 | 2 | H | 5-NH₂ | Et |
| 32 | NH | 0 | 2 | 4-HO | H | Et |
| 33 | NH | 0 | 2 | 4-Me₂NCH₂CH₂NH | H | Et |
| 34 | NH | 0 | 2 | 4-Me | H | Et |
| 35 | NH | 0 | 2 | 4-NH₂ | H | Et |
| 36 | NAc | 0 | 2 | 4-Me | H | Et |
| 37 | S | 0 | 2 | H | H | Et |
| 38 | S | 0 | 2 | 4-Me | H | Et |
| 39 | S | 0 | 2 | 4-HO | H | Et |
| 40 | S | 0 | 2 | 4-NO₂ | H | Et |
| 41 | S | 0 | 2 | 4-NH₂ | H | Et |
| 42 | S | 0 | 2 | 4-NH₂NH | H | Et |
| 43 | S | 0 | 2 | 4-Me₂NCH₂CH₂O | H | Et |
| 44 | S | 0 | 2 | 4-Et₂NCH₂CH₂NH | H | Et |
| 45 | S | 0 | 2 | H | 5-NH₂ | Et |
| 46 | S | 1 | 1 | 4-Me | H | Et |
| 47 | S | 1 | 1 | 4-HO | H | Et |
| 48 | S | 1 | 1 | H | 5-NH₂ | Et |
| 49 | S | 1 | 1 | 4-NH₂ | H | Et |
| 50 | O | 0 | 2 | 4-NH₂ | H | Et |
| 51 | O | 0 | 2 | 4-Me | H | Et |
| 52 | O | 0 | 2 | 4-MeO | H | Et |
| 53 | O | 0 | 2 | 4-HO | H | Et |
| 54 | O | 1 | 1 | 4-Br | H | Et |
| 55 | O | 1 | 1 | 4-HO | H | Et |
| 56 | CH₂ | 0 | 2 | H | H | Et |
| 57 | CH₂ | 0 | 2 | 4-HO | H | Et |
| 58 | CH₂ | 0 | 2 | 4-Me | H | Et |
| 59 | CH₂ | 0 | 2 | 4-MeO | H | Et |
| 60 | CH₂ | 0 | 2 | 4-Cl | H | Et |
| 61 | CH₂ | 0 | 2 | 4-Me₂NCH₂CH₂O | H | Et |
| 62 | CH₂ | 0 | 2 | 4-NO₂ | H | Et |
| 63 | CH₂ | 0 | 2 | 4-NH₂ | H | Et |
| 64 | CH₂ | 0 | 2 | 4-NH₂NH | H | Et |
| 65 | CH₂ | 0 | 2 | 4-dimethyl-hydradino | H | Et |
| 66 | CH₂ | 0 | 2 | 4-(pyrrolidinone-3-yl)amino | H | Et |
| 67 | CH₂ | 0 | 2 | 4-(morphorine-4-yl)amino | H | Et |
| 68 | CH₂ | 0 | 2 | 4-(piperidine-1-yl)amino | H | Et |
| 69 | CH₂ | 0 | 2 | 4-(piperazine-1-yl)amino | H | Et |
| 70 | CH₂ | 0 | 2 | 4-(4-methyl piperazine-1-yl)amino | H | Et |
| 71 | CH₂ | 0 | 2 | 4-(4-methyl piperidine-1-yl)amino | H | Et |
| 72 | CH₂ | 0 | 2 | 4-(4-methyl-piperazine-1-)yl | H | Et |
| 73 | CH₂ | 0 | 2 | 4-(4-amino-piperazine-1-)yl | H | Et |
| 74 | CH₂ | 0 | 2 | 4-(4-amino-piperidine-1-)yl | H | Et |
| 75 | CH₂ | 0 | 2 | 4-(4-piperidine 4-yl)amino | H | Et |
| 76 | CH₂ | 0 | 2 | 4-(4-azetidine-3-yl)amino | H | Et |
| 77 | CH₂ | 0 | 2 | 4-(3-amino-azetidine-1-yl) | H | Et |
| 78 | CH₂ | 0 | 2 | 4-NH₂CH₂CH₂O | H | Et |
| 79 | CH₂ | 0 | 2 | 4-(piperazine-1-yl) | H | Et |
| 80 | CH₂ | 0 | 2 | 4-NH₂CH₂CH₂NH | H | Et |
| 81 | CH₂ | 0 | 2 | 4-Me₂NCH₂CH₂NH 3-yl)amino | H | Et |
| 82 | CH₂ | 0 | 2 | H | 5-(pyrrolidine-3-yl)amino | Et |
| 83 | CH₂ | 0 | 2 | H | 5-(morphorine-4-yl)amino | Et |
| 84 | CH₂ | 0 | 2 | H | 5-(piperazine-1-yl) | Et |

-continued

| No. | % | m | n | R₁ | R₂ | R₃ |
|---|---|---|---|---|---|---|
| 85 | CH₂ | 0 | 2 | H | 5-(4-methyl-piperazine-1-yl) | Et |
| 86 | CH₂ | 0 | 2 | H | 5-(piperidine-1-yl)amino | Et |
| 87 | CH₂ | 0 | 2 | H | 5-NH₂CH₂CH₂NH | Et |
| 88 | CH₂ | 0 | 2 | H | 5-Me₂NCH₂CH₂NH | Et |
| 89 | CH₂ | 0 | 2 | H | 5-CH₃ | Et |
| 90 | CH₂ | 0 | 2 | H | 5-NH₂CH₂ | Et |
| 91 | CH₂ | 0 | 2 | H | 5-HOCH₂ | Et |
| 92 | CH₂ | 0 | 2 | H | 5-HO | Et |
| 93 | CH₂ | 0 | 2 | H | 5-NH₂NH | Et |
| 94 | CH₂ | 0 | 2 | H | 5-NH₂ | Et |
| 95 | CH₂ | 0 | 2 | 4-CH₃ | 5-HO | Et |
| 96 | CH₂ | 0 | 2 | 4-CH₃ | 5-NH₂ | Et |
| 97 | CH₂ | 0 | 2 | 4-CH₃ | 5-(piperazine-1-yl) | Et |
| 98 | CH₂ | 0 | 2 | 4-HO | 5-(4-methyl-piperazine-1-yl) | Et |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent:

1. A compound represented by the following formula

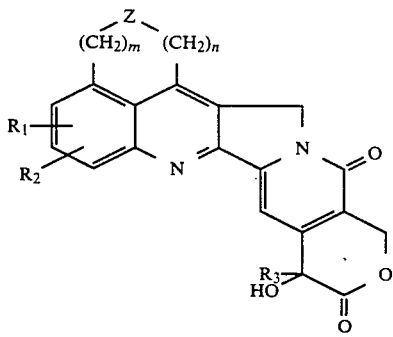

(I)

wherein R₁ and R₂ independently represent hydrogen atoms, hydroxyl groups, C₁₋₆ alkyl groups, C₁₋₆ alkenyl groups, C₁₋₆ alkynyl groups, C₁₋₆ alkoxyl groups, C₁₋₆ aminoalkoxyl groups, halogen atoms, nitro groups, cyano groups, mercapto groups, C₁₋₆ alkylthio groups, C₁₋₆ hydroxyalkyl groups, C₁₋₆ halogenoalkyl groups, C₁₋₆ cyanoalkyl groups, C₁₋₆ nitroalkyl groups, amino groups which may contain protective groups, C₁₋₆ aminoalkyl groups which may contain protective groups or C₁₋₆ alkyl groups, C₁₋₆ aminoalkylamino groups which may contain protective groups or C₁₋₆ alkyl groups at the amino-position, heterocyclic C₁₋₆ alkyl groups which may contain C₁₋₆ alkyl, C₁₋₆ alkoxyl, amino, halogeno, nitro, or cyano groups, heterocyclic C₁₋₆ alkylamino groups which may contain C₁₋₆ alkyl, C₁₋₆ alkoxyl, amino (which may contain protective groups), halogeno, nitro, cyano groups, or protective groups, amino-heterocyclic groups which may contain protective groups or C₁₋₆ alkyl groups at the nitrogen atom of the heterocyclic ring moiety or amino position, heterocyclic-amino groups which may contain protective groups of C₁₋₆ alkyl groups at the nitrogen atom of the heterocyclic ring moiety or amino position, carbamoyl groups which may contain protective groups or C₁₋₆ alkyl groups, heterocyclic carbonyl groups which may contain C₁₋₆ alkyl, C₁₋₆ alkoxyl, amino, hydroxyl, halogeno, nitro, or cyano groups, R₃ represents an C₁₋₆ alkyl group, Z represents O, S, CH—R₄ (R₄ stands for a hydrogen atom or a C₁₋₆ alkyl group), or N—R₅ (R₅ stands for a hydrogen atom, a C₁₋₆ alkyl group, or a protective group for the amino group), and m and n independently represent 0, 1 or 2 provided that m and n are not both equal to 2, and wherein said heterocyclic group is selected from the group consisting of azetidine, pyrrolidine, piperidine, piperazine, imidazoline, and morpholine, and wherein said protective group is selected from the group consisting of acetyl, formyl, trityl, tert-butoxycarbonyl, and p-methoxybenzoyloxycarbonyl.

2. The compound as claimed in claim 1, wherein said compound has S-type configuration with respect to the substituent groups at F-ring in said formula (I).

3. A compound which is selected from the group consisting of 9-ethyl-2,3-dihydro-4,9-dihydroxy-1H,12H-benzo [de]pyrano[3',4':6,7]indolizino[1,2-b]quinoline-10,13 (9H,15H)-dione; 9-ethyl-1,2-dihydro-9-hydroxy-4-methyl-12H-pyrano [4,3,2-de]-pyrano[3',4':6,7]-indolizino [1,2-b]quinoline-10,13(9H,15H)-dione; 9-ethyl-1,2-dihydro-9-hydroxy-4-methyl-12H-thiino[4,3,2-de]pyrano[3', 4':6,7]indolizino[1,2-b]quinoline-10,13 (9H,15H)-dione; 9-ethyl-1,2-dihydro-9-hydroxy-4-methyl-3H,12H-pyrano[3',4':6,7]indolizino[1,2-c]benzo[ij][2,7]naphthilidine-10,13(9H,15H)-dione; 4-chloro-9-ethyl-2,3-dihydro-9-hydroxy-1H,12H-benzo[de]pyrano[3',4':6.7]indolizino[1,2-b]quinoline-l10,13(9H,15H)-dione; 8-ethyl-1,2-dihydro-3,8-dihydroxy-11H-cyclopenta[de]-pyrano[3',4':6,7]indolizino[1,2-b]-quinoline-9,12 (8H,14H)-dione; 9-ethyl-1,2-dihydro-4,9-dihydroxy-12H-pyrano[4,3,2-de]pyrano[3',4':6,7]-indolizino[1,2-b]-quinoline-10,13(9H,15H)-dione; 4-cyano-1,2-dihydro-9-ethy-9-hydroxy-12H-thiino[4,3,2 -de]pyrano[3',4':6,-7]indolinzino[1,2-b]quinoline-10,13(9H,15H)-dione; ,4-amino-1,2-dihydro-9-ethyl-9-hydroxy-12H-thiino[4,2,3-de]pyrano[3',4':6,7[-indolizino[1,2,-b]quinoline-10,13(9H,15H)-dione; and 1,2-dihydro-9-ethyl-9-hydroxy-12H-thinno[4,3,2,-de]pyrano[3',4':6,7]indolizino[1,2-b]quinoline-10,13(9H,15H)-dione.

* * * * *